(12) United States Patent
Gledhill, III et al.

(10) Patent No.: US 9,909,579 B2
(45) Date of Patent: Mar. 6, 2018

(54) OVERMOLDED TUBING ASSEMBLY AND ADAPTER FOR A POSITIVE DISPLACEMENT PUMP

(71) Applicant: Blue-White Industries, Ltd., Huntington Beach, CA (US)

(72) Inventors: Robert Gledhill, III, Huntington Beach, CA (US); John Nguyen, Fountain Valley, CA (US); Steven Lee Smith, Costa Mesa, CA (US)

(73) Assignee: Blue-White Industries, Ltd., Huntington Beach, CA (US)

( * ) Notice: Subject to any disclaimer, the term of this patent is extended or adjusted under 35 U.S.C. 154(b) by 470 days.

(21) Appl. No.: 14/573,460

(22) Filed: Dec. 17, 2014

(65) Prior Publication Data
US 2015/0354555 A1 Dec. 10, 2015

Related U.S. Application Data

(60) Provisional application No. 62/009,858, filed on Jun. 9, 2014.

(51) Int. Cl.
*F04B 43/12* (2006.01)

(52) U.S. Cl.
CPC ...... *F04B 43/1261* (2013.01); *F04B 43/1284* (2013.01); *F04B 43/1292* (2013.01); *Y10T 29/49238* (2015.01)

(58) Field of Classification Search
CPC ....... F16L 39/02; F16L 11/22; F04B 43/1292; F04B 43/1261; F04B 43/1284
USPC .................. 417/474, 475, 476, 477.1–477.9, 417/477.11–477.14, 478, 479
See application file for complete search history.

(56) References Cited

U.S. PATENT DOCUMENTS

| | | | |
|---|---|---|---|
| 2,877,028 A | * | 3/1959 | Knight .................... F16L 39/02 285/124.4 |
| 2,916,055 A | | 12/1959 | Brumbach |
| 3,429,266 A | | 2/1969 | Jones |

(Continued)

FOREIGN PATENT DOCUMENTS

| | | | |
|---|---|---|---|
| GB | 2115498 | | 9/1983 |
| GB | 2115498 A | * | 9/1983 .......... F04B 43/1292 |

OTHER PUBLICATIONS

Omegaflex Polyurethan Ether Tubing and Spec Sheet, www.omega.com/pptst/tyuth.html; archive dated Jan. 26, 2009 accessed via Waybackmachine.

(Continued)

*Primary Examiner* — Nathan Zollinger
(74) *Attorney, Agent, or Firm* — Knobbe Martens Olson & Bear, LLP

(57) ABSTRACT

A tubing assembly is provided that can comprise a plurality of tubes or lumens that can be disposed within a head of a peristaltic pump. The tubing assembly can provide a flow rate or volume capacity that is generally equal to or greater than that achieved with a comparable prior art tube while operating at higher pressures than that possible using the prior art tube. Further, in accordance with some embodiments, the tubing assembly can achieve a longer working life than a comparable prior art tube, and the load on the pump motor can be reduced such that the pump life is increased and/or a larger pump motor is not required to achieve such advantageous results.

28 Claims, 29 Drawing Sheets

(56) References Cited

U.S. PATENT DOCUMENTS

| | | |
|---|---|---|
| 3,723,030 A | 3/1973 | Gelfand |
| 3,737,251 A | 6/1973 | Berman et al. |
| 3,740,173 A | 6/1973 | Natelson |
| 3,791,777 A | 2/1974 | Papoff et al. |
| 3,832,096 A | 8/1974 | Gelfand |
| 3,907,022 A | 9/1975 | Gulich |
| 4,289,459 A | 9/1981 | Neeley et al. |
| 4,473,173 A | 9/1984 | DeGroff et al. |
| 4,522,570 A | 6/1985 | Schartz |
| 4,604,038 A | 8/1986 | Belew |
| 4,648,812 A | 3/1987 | Kobayashi et al. |
| 4,722,559 A * | 2/1988 | Bongartz ............ F16L 41/03 239/600 |
| 4,834,630 A | 5/1989 | Godwin |
| 4,878,622 A | 11/1989 | Jamison et al. |
| 4,982,903 A | 1/1991 | Jamison et al. |
| 5,025,270 A | 6/1991 | Umezawa |
| 5,037,274 A | 8/1991 | Holmes et al. |
| 5,257,917 A | 11/1993 | Minarik et al. |
| 5,443,451 A | 8/1995 | Chapman et al. |
| 5,460,493 A | 10/1995 | Deniega et al. |
| 5,846,061 A | 12/1998 | Ledebuhr et al. |
| 5,870,805 A | 2/1999 | Kandler et al. |
| 5,988,801 A | 11/1999 | Coiner |
| 6,068,370 A | 5/2000 | Miller et al. |
| 7,118,203 B2 | 10/2006 | Davis et al. |
| 7,144,231 B2 | 12/2006 | Davis |
| 7,241,119 B2 | 7/2007 | Harada |
| 7,467,932 B2 | 12/2008 | Schann et al. |
| 7,513,757 B2 | 4/2009 | Gibson et al. |
| 7,591,639 B2 | 9/2009 | Kent |
| 8,393,879 B2 | 3/2013 | Kent |
| 2004/0022656 A1 | 2/2004 | Anderson |
| 2006/0002799 A1 | 1/2006 | Schann et al. |
| 2009/0053084 A1 | 2/2009 | Klein |
| 2011/0180172 A1 | 7/2011 | Gledhill, III et al. |
| 2014/0271293 A1 | 9/2014 | Gledhill, III et al. |

OTHER PUBLICATIONS

Bioprene High performance TPE and Spec Sheet, www.watson-marlow.co.uk/Tubing/bioprene.htm; archive dated Feb. 6, 2009 accessed via Waybackmachine.

* cited by examiner

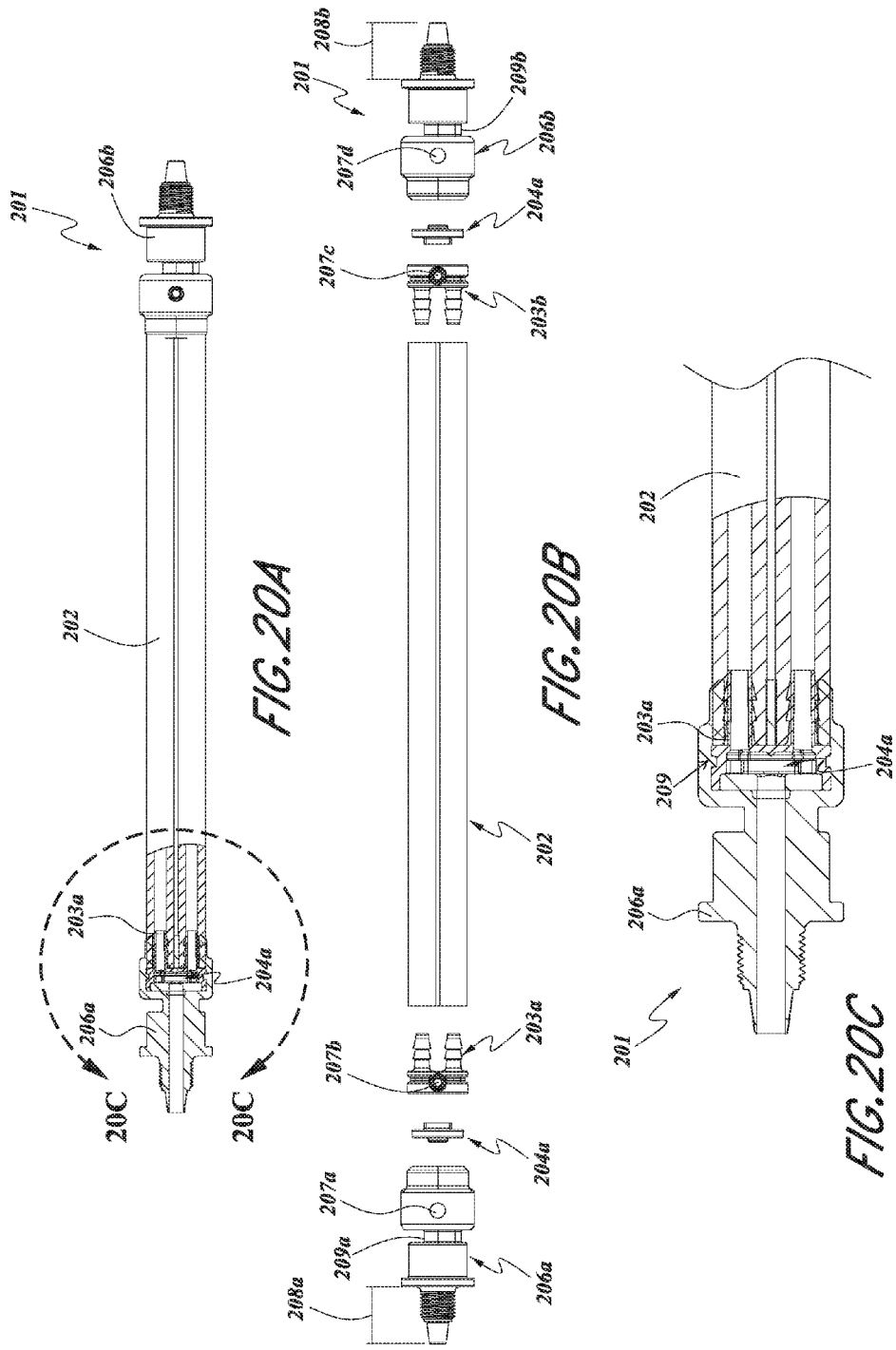

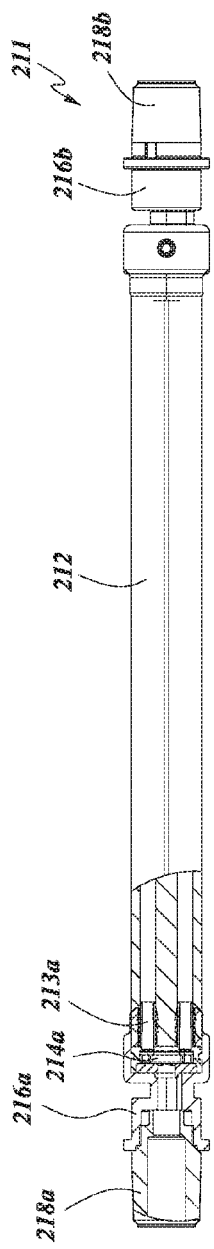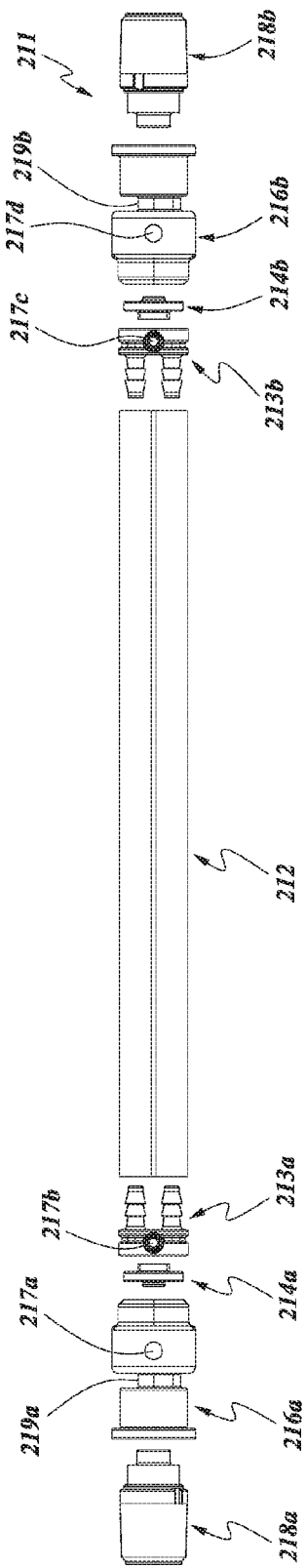
FIG. 21A
FIG. 21B

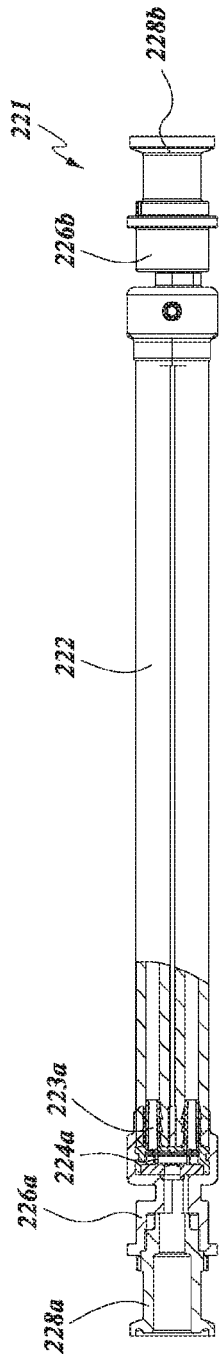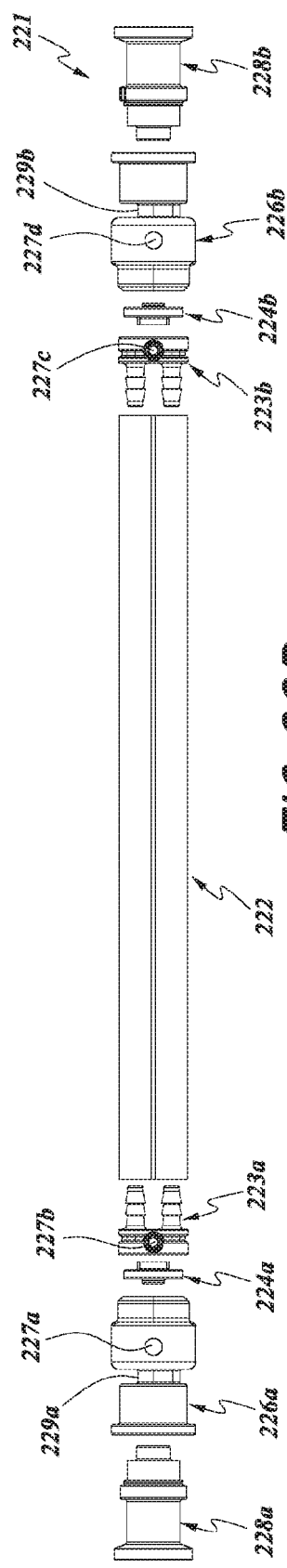

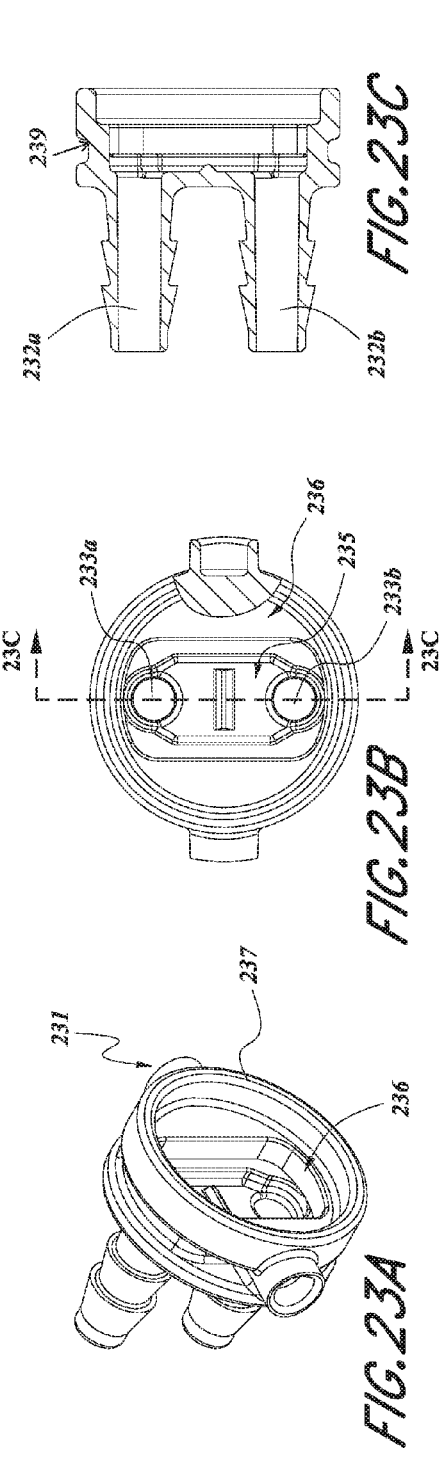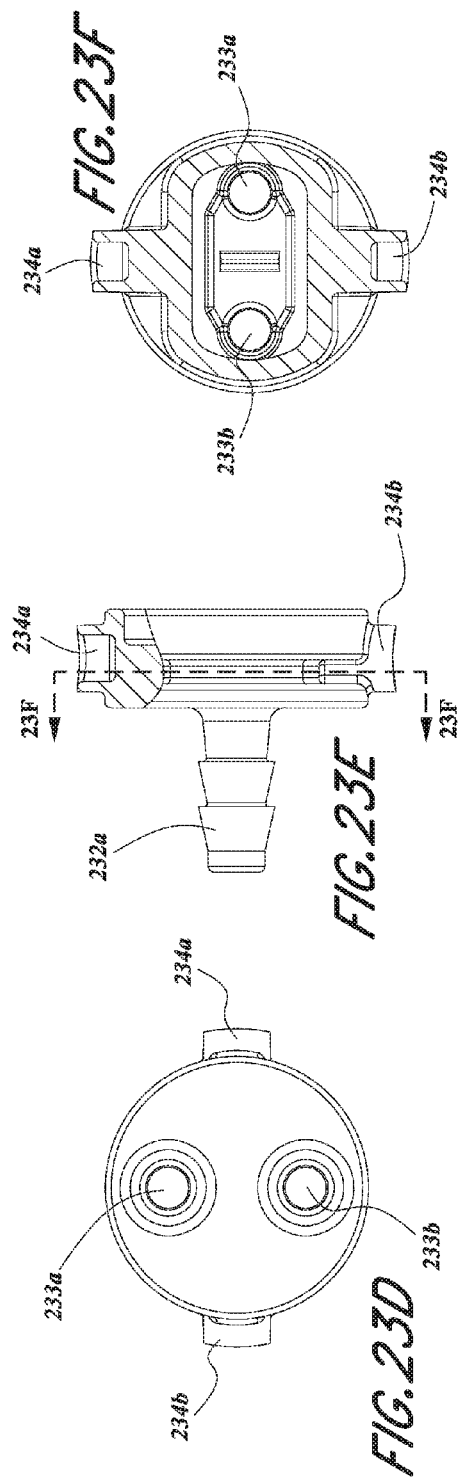

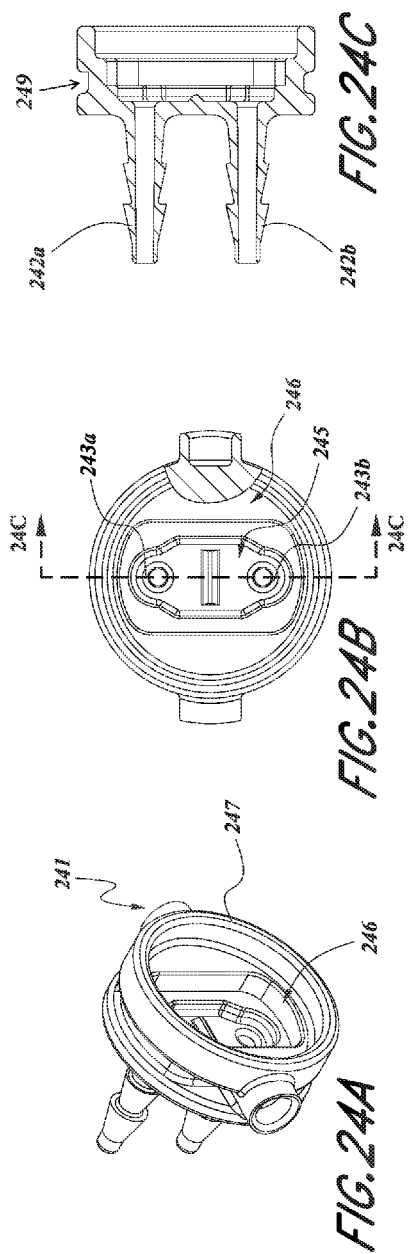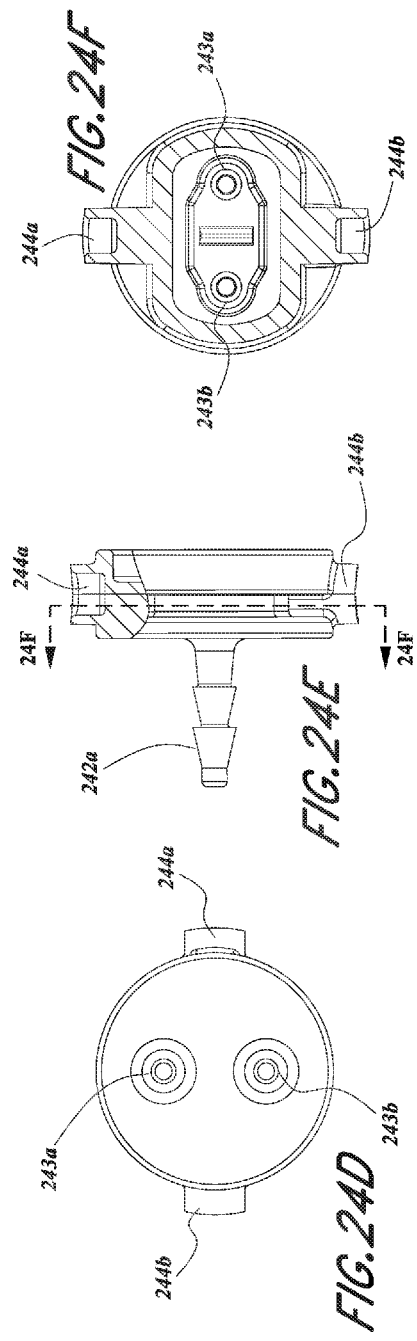

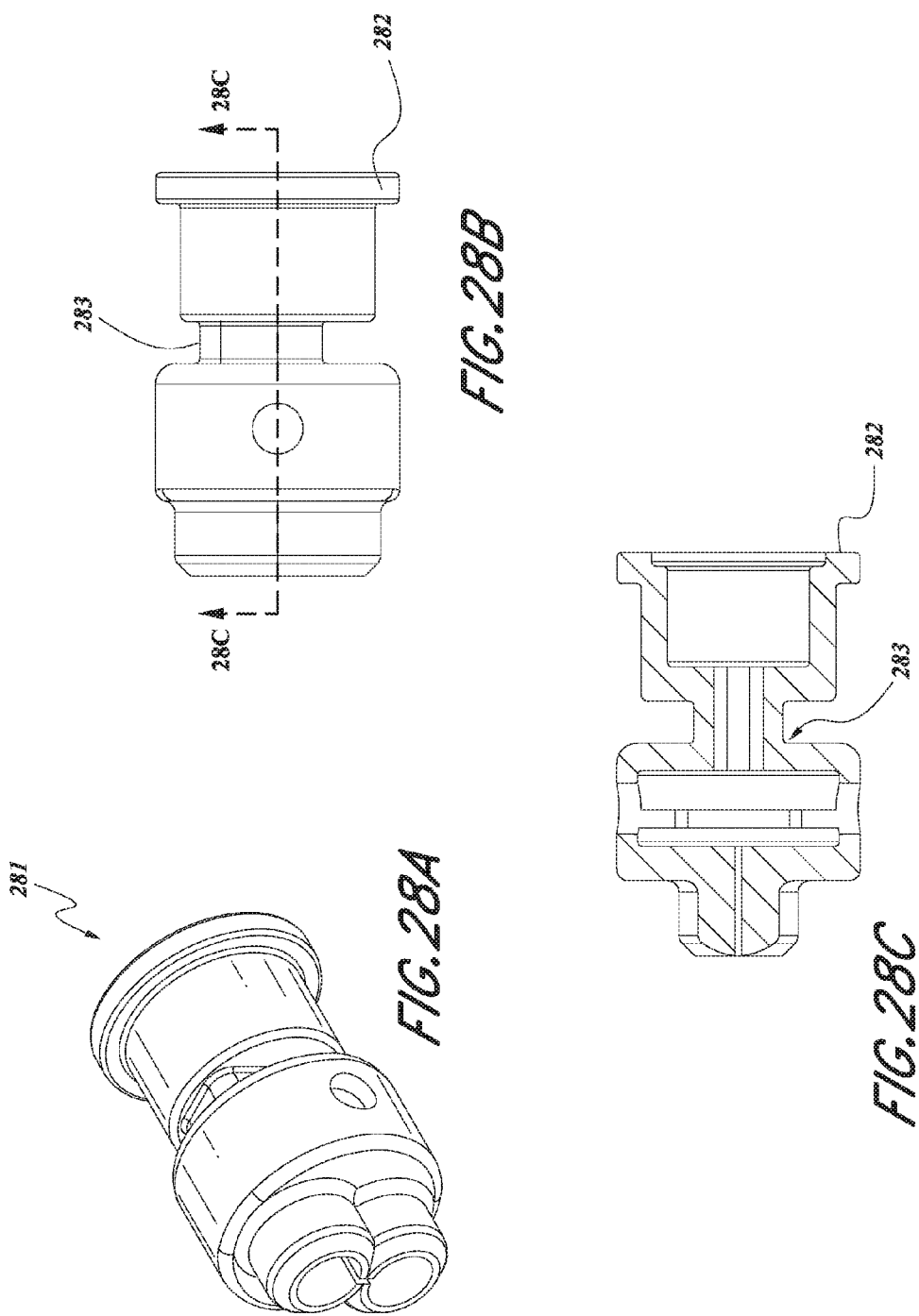

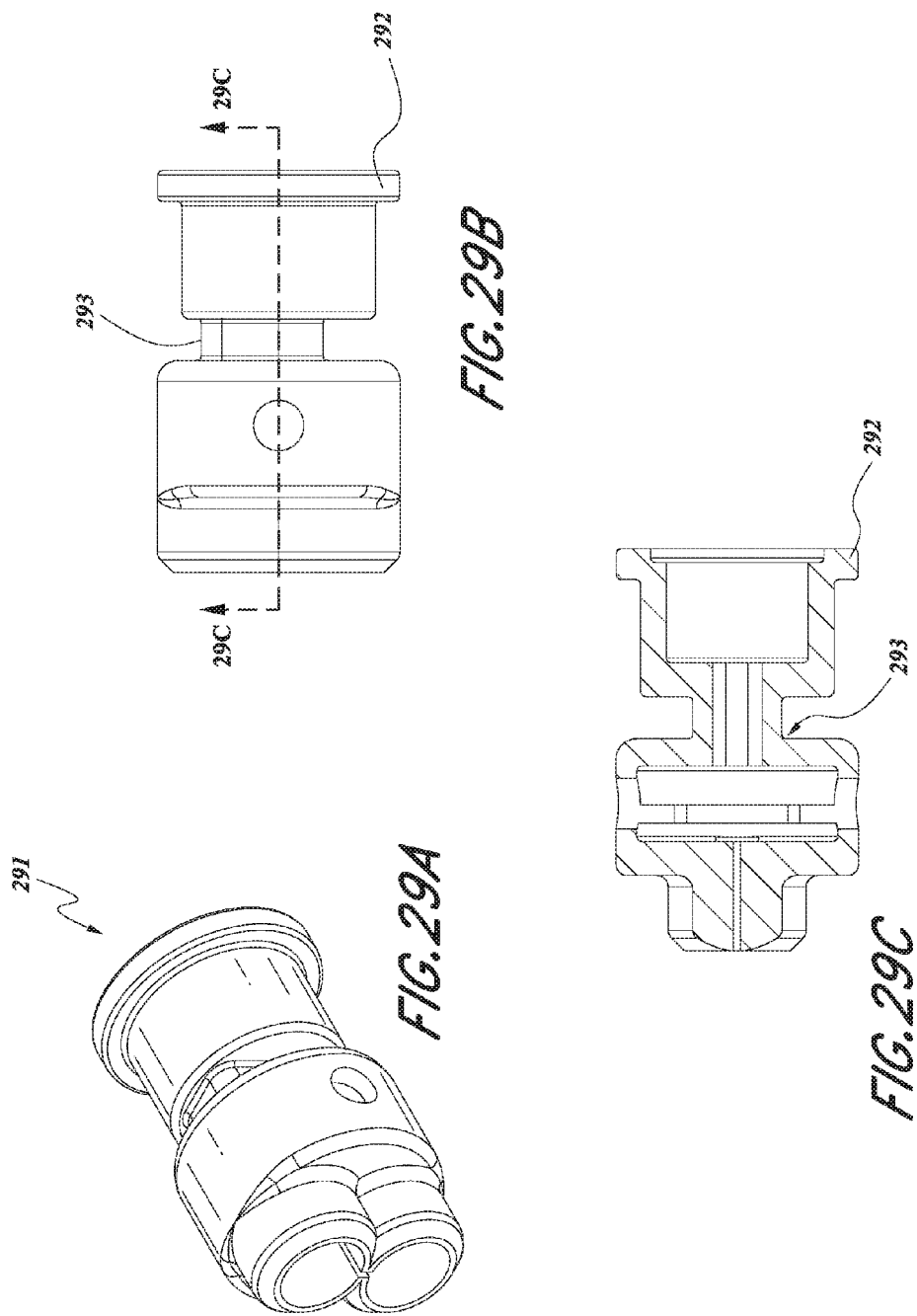

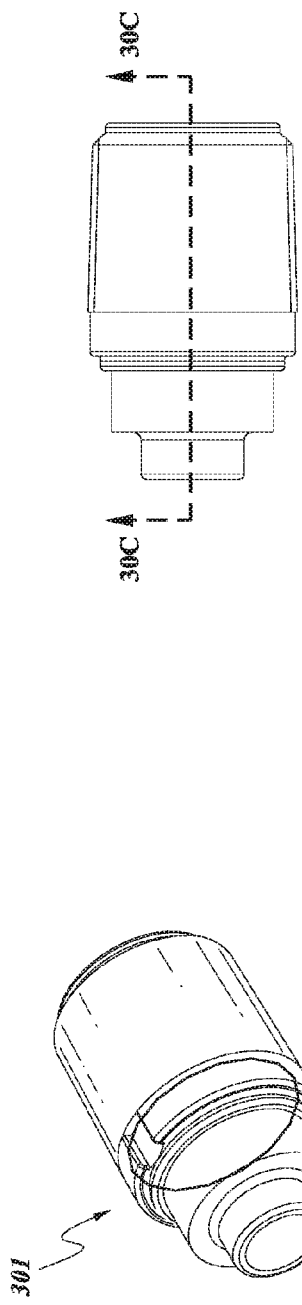
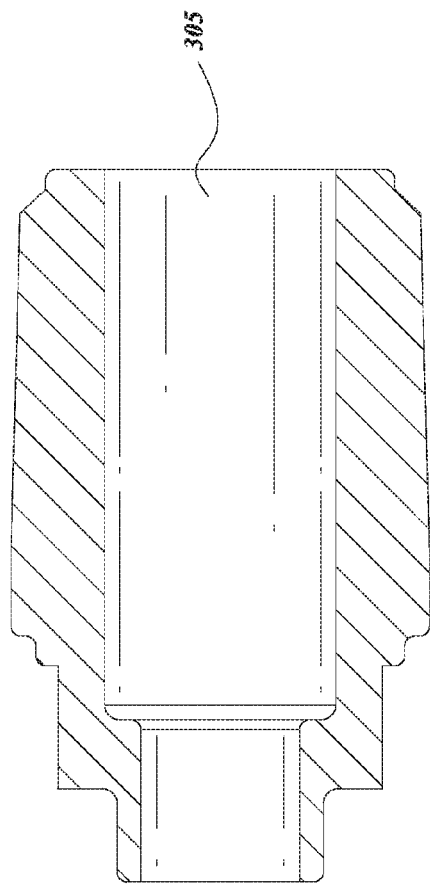
FIG. 30A
FIG. 30B
FIG. 30C

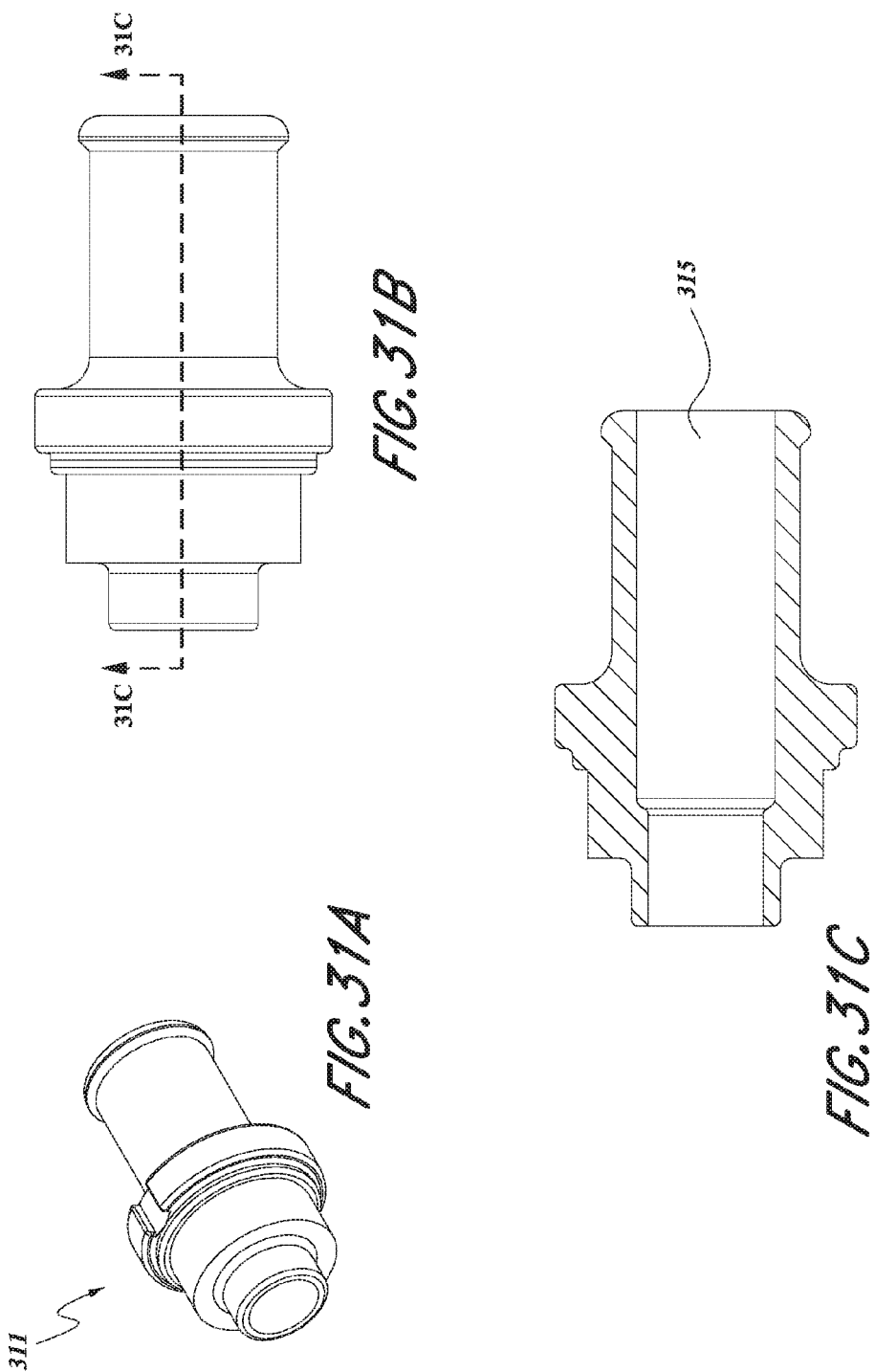

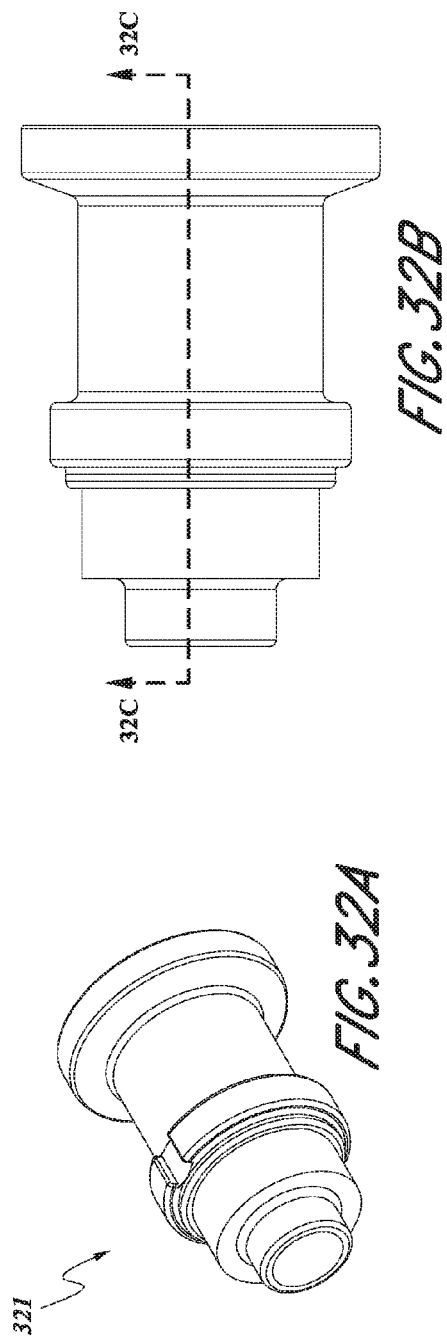

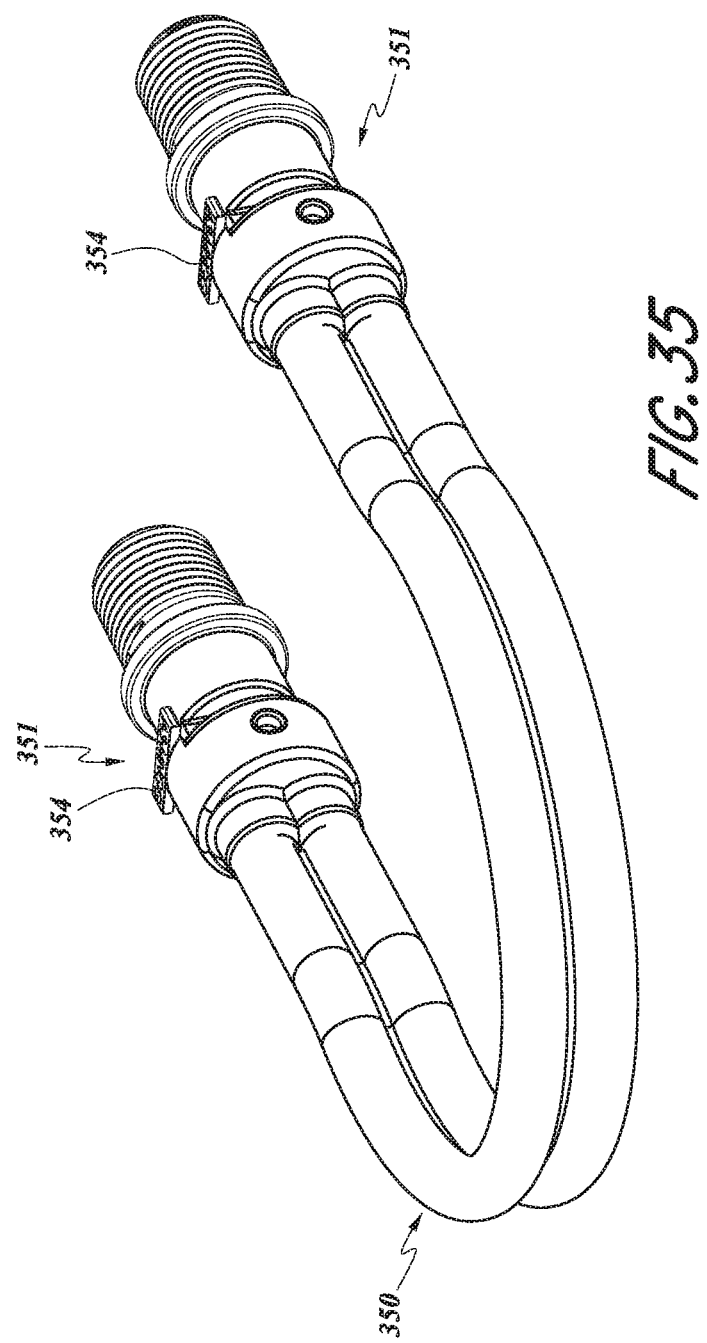

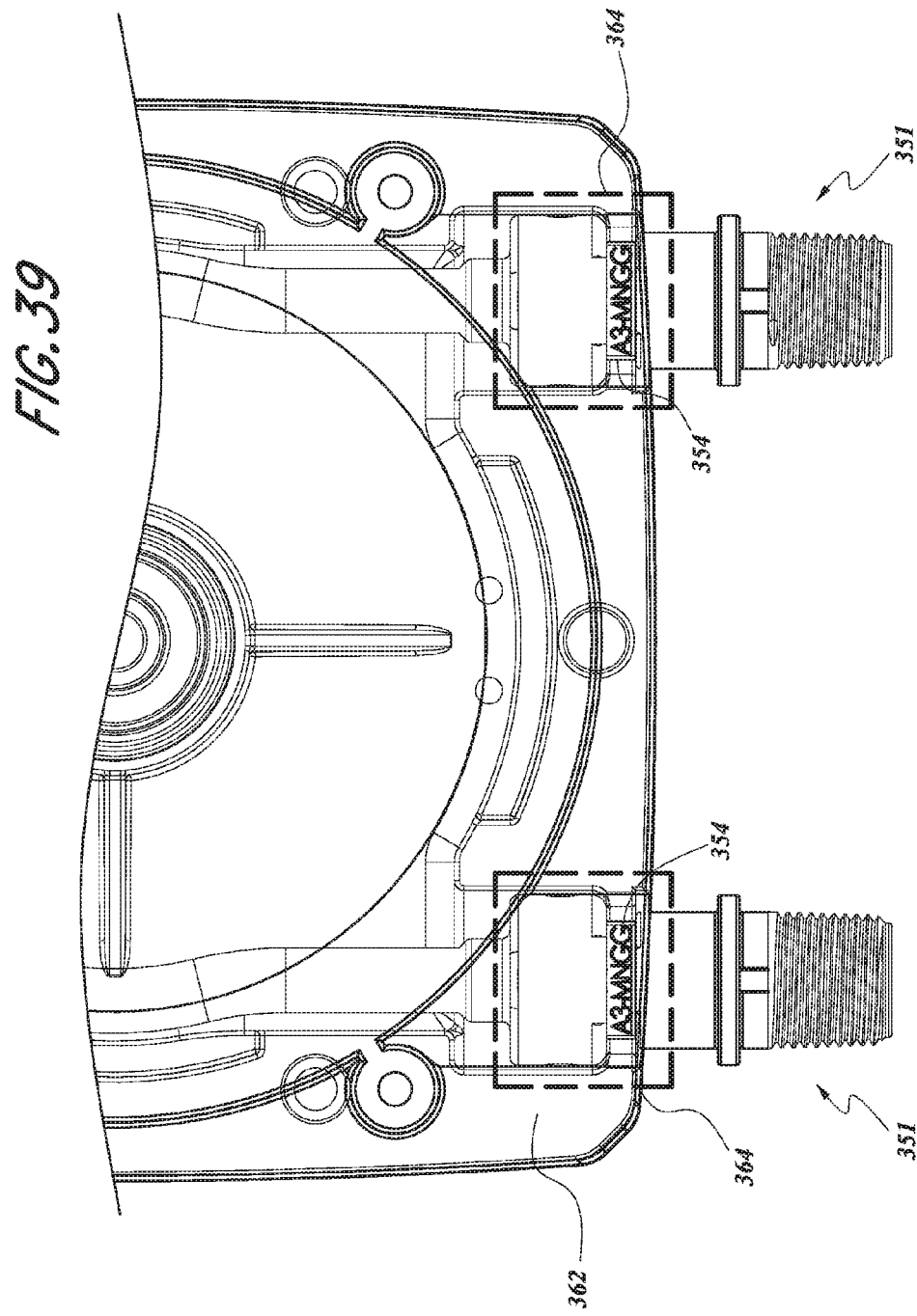

OVERMOLDED TUBING ASSEMBLY AND ADAPTER FOR A POSITIVE DISPLACEMENT PUMP

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims the benefit of U.S. Provisional Patent Application No. 62/009,858, entitled "OVERMOLDED TUBING ASSEMBLY AND ADAPTER FOR A POSITIVE DISPLACEMENT PUMP," filed on Jun. 9, 2014, which is hereby incorporated by reference in its entirety.

FIELD OF THE INVENTION

The present inventions relate to tubing assemblies, and more specifically to tubing assemblies for use with peristaltic pumps.

DESCRIPTION OF THE RELATED ART

A peristaltic roller pump typically has two or more rollers, but may have other configurations. The rollers are generally spaced circumferentially evenly apart and are mounted on a rotating carrier that moves the rollers in a circle. A length of flexible tubing may be placed between the rollers and a semi-circular wall. In medical and lab applications, the tubing can be a relatively soft and pliable rubber tubing. For relatively high-pressure industrial applications, however, the tubing can be exceedingly durable and rigid, albeit flexible under the high pressure of the rollers.

In use, the rollers rotate in a circular movement and compress the tubing against the wall, squeezing the fluid through the tubing ahead of the rollers. The rollers are configured to almost completely occlude the tubing, and operate essentially as a positive displacement pump, each passage of a roller through the semicircle pumps the entire volume of the fluid contained in the tubing segment between the rollers.

As a positive displacement pump, relatively high positive pressures can be generated at the pump outlet. Peristaltic roller pumps are typically driven by a constant speed motor that draws fluid at a substantially constant rate.

Typically, a large inventory of peristaltic pump tubing assembly adapters must be held to accommodate customer requirements. In most cases, the entire tubing assembly must be replaced if a customer changes the external fitting. Furthermore, traditional tubing assemblies for a peristaltic pump incorporate a metal clamp to hold the tubing to the adapter and prevent leakage. These assemblies are susceptible to metal corrosion due to the leakage of fumes into the pump head housing.

SUMMARY

The present inventions relate to pumps and tubing assemblies that are configured to pump fluids at high pressures and high flow rates. More particularly, the tubing assemblies can comprise multiple small diameter tubes that replace the traditional single large diameter hose in peristaltic pumps. In particular, embodiments disclosed herein can enable pumping against high pressures while providing a high flow rate, increased tube life, increased drive efficiency, lower replacement cost, lower energy consumption, cooler operating temperatures, and reduced operating and maintenance costs. Additionally, the tubing assemblies can comprise an interchangeable adapter system that may require less inventory cost and take up less inventory space. In some embodiments, the adapter system may include a plurality of pump tubing grippers or locks, a plurality of adapter/external system interfaces, and a plurality of end fittings. These pieces may be used interchangeably to fit a variety of tubing profiles, including single or dual tube or multiple lumen tubing, and customer requirements. All of these advantages are achieved while implementing designs that contrast with the traditional industry standard and knowledge. Similar tubing and adapter designs are disclosed in U.S. patent application Ser. No. 14/195,678, entitled "HIGH PRESSURE, HIGH FLOW RATE TUBING ASSEMBLY AND ADAPTER FOR A POSITIVE DISPLACEMENT PUMP," filed on Mar. 3, 2014, which is hereby incorporated by reference in its entirety.

In many facilities, typical water pressures can range from 60 to 85 PSI. Most municipalities prefer chemical pumps that can exceed system pressure by at least 20%. Some traditional peristaltic "tube" pumps (which use a single conduit having a diameter of less than 1 inch, referred to as a "tube") meet the requirements of some water treatment facilities that have small to medium chemical injection demands. However, system pressures and chemical flow rates often exceed the capabilities of existing peristaltic "tube" pumps. Consequently, operators must use larger peristaltic "hose" pumps (which, in contrast to peristaltic "tube" pumps, use a single conduit with a diameter of at least 1 inch or more, referred to as a "hose" because it is larger than a "tube"). Peristaltic hose pumps are considerably more expensive to operate (often three times more) because they use large, high-torque, high-horsepower AC drives.

Although peristaltic pumps have gained widespread popularity, the effectiveness of current peristaltic pumps is severely limited by the design of the tube or hose. The present Applicants spent considerable time and resources researching and redesigning large tubes and hoses for use in high pressure, high flow rate applications. The general rule in industry has always been that the larger diameter of the tube or hose, the higher the pump flow rate (or output). Further, high-pressure industrial peristaltic pumps typically require durable, stiff tubing in order to withstand high pressures. However, using a large diameter tube or hose at high pressure also requires a larger wall thickness in order to withstand the high pressure and avoid "ballooning." Tubing in a peristaltic pump tends to expand or balloon at the outlet side where system pressure is exerted, and the effects of the ballooning and relaxing of the tubing can build up over time. As the tube size increases in diameter (in order to increase flow rate), the ballooning effect becomes more prevalent. In order to overcome the ballooning problem, the wall thickness of the tubing must be increased, which in turn, causes more resistance to the pumping unit, adding more load to the pump drive unit. These challenges only increase as the required operating pressure is increased. Accordingly, the industry solution prior to the development of the present inventions was to provide a pump with a very powerful motor that can rotate the rollers over a single large diameter, large wall thickness, stiff tube or hose and deliver fluid at high pressures.

In contrast to prior art techniques and applications, some embodiments disclosed herein reflect the realization that instead of using a single large diameter, large wall thickness, stiff tube or hose in a peristaltic pump, high pressures and high flow rates can be achieved with a peristaltic tube pump that uses a system of two or more tubes in which each tube has a smaller diameter and a specific relationship between tube wall thickness and tube durometer. As a result, the pump motor can be much smaller and more efficient than the traditional counterpart peristaltic hose pump that uses a large, stiff tube with a large wall thickness. Moreover, some embodiments are capable of pumping at high pressures and high flow rates while also resulting in increased tube life, increased drive efficiency, lower replacement cost, lower energy consumption, cooler operating temperatures, and reduced operating and maintenance costs. Further, embodiments disclosed herein can deliver fluid at pressures and flow rates that well exceed industry demands. For example, some embodiments can deliver fluid at pressures at or well above 100 PSI while achieving the industry-required flow rates.

Accordingly, some embodiments reflect realizations that in contrast to prior art peristaltic pumps and systems that use a single larger, stiff tube, a peristaltic pump and system using multiple smaller tubes can handle higher pressures, have a longer tube life than a single larger tube, have better memory retention than a single larger tube, and be more energy efficient than a single larger tube. Thus, while the industry has sought to increase fluid output by increasing the size of the tube and increasing the RPM of the motor, some embodiments disclosed herein reflect a contrary view and achieve superior results by using multiple tubes with smaller diameters.

For example, some embodiments disclosed herein reflect the realization that due to the continual cycles of compression and relaxation produced by each pass of the rotating cam, larger diameter tubes (hoses) flatten out sooner, causing a lower flow rate after a short amount of time. Some embodiments disclosed herein also reflect the realization that the ballooning effect can be minimized by using smaller tubes, and that a pump can generally overcome this phenomenon without challenges. Furthermore, some embodiments reflect the realization that smaller tubes tend to retain original memory for an extended amount of time (much longer than a larger diameter tube), resulting in higher accuracy and longer tube life. Moreover, some embodiments reflect the realization that unlike traditional small diameter tubing (which has not been used in high-pressure applications and have a low pressure rating), embodiments can be provided in which a small diameter tube has a desired tube wall thickness and/or desired tube durometer, and/or a desired ratio of tube wall thickness to tube durometer.

Further, some embodiments disclosed herein reflect the realization that there are various potential hazards associated with running a peristaltic pump with large diameter tubing (hose). For example, as noted above, having a large wall thickness to achieve high pressures can cause additional load to the pump drive. Tube diameter expansion (ballooning) can occur on pressure side of pump, which can require additional pump drive load to overcome tube diameter expansion (ballooning) and may result in early tube rupture. In pumps having a glycerin-filled pump head (which is used to reduce friction and heat), tube rupture can cause glycerin to enter the fluid path and contaminate the system.

Additional embodiments disclosed herein illustrate a clamp-less adapter and tubing assembly for a peristaltic pump. Single or multi-lumen tubing assemblies may be manufactured with a variety of clamp-less adapters depending on customer requirements. The clamp-less adapter and tubing assembly takes up less space within the pump head housing than traditional clamped adapter and tube assemblies. In the case of multiple lumen tubing assemblies, the clamp-less style adapter assembly allows the tubes to be closer to each other, without interference from bulky metal clamps.

In one embodiment, a tubing and adapter assembly for a peristaltic pump is disclosed. The tubing and adapter assembly includes an elongate body defining a longitudinal axis, a first end, and a second end, the elongate body having a plurality of lumens extending along the longitudinal axis, each lumen being surrounded by a tube wall, the plurality of lumens extending from the first end to the second end such that the first end is in fluid communication with the second end of the elongate body; a first tube gripper having a plurality of prongs defining cylindrical openings such that each of said plurality of prongs grip an interior surface of a tube wall defining one of the plurality of lumens adjacent said first end of the body; a second tube gripper having a plurality of prongs defining cylindrical openings such that each of said plurality of prongs grip an interior surface of a tube wall defining one of the plurality of lumens adjacent said second end of the body; a first external system interface having an annular surface defining a first flow passage, a first tubing interface portion, a first pump interface portion, and a first mounting interface portion; a second external system interface having an annular surface defining a second flow passage, a second tubing interface portion, a second pump interface portion, and a second mounting interface portion; wherein the first and second external system interfaces are molded over the first and second tube grippers respectively to form a seal on an exterior surface of the tube walls defining the plurality of lumens such that a rotor of the peristaltic pump can operate against the tubing and adapter assembly for pumping fluid through the tubing and adapter assembly. In some embodiments, the first external system interface is one of a hose barb adapter, threaded adapter, sanitary adapter, and quick-release adapter. In some embodiments, the second external system interface is one of a hose barb adapter, threaded adapter, sanitary adapter, and quick-release adapter. In some embodiments, the first external system interface is the same type of interface as the second external system interface. In some embodiments, the first external system interface is not the same type of interface as the second external system interface. In some embodiments, a first tubing interface is coupled to the first external system interface by one of spin welding, sonic welding, glue, threaded connection, and one or more mechanical fasteners. In some embodiments, a second tubing interface is coupled to the second external system interface by one of spin welding, sonic welding, glue, threaded connection, and one or more mechanical fasteners. In some embodiments, the tubing assembly comprises three lumens. In some embodiments, the tubing assembly comprises two lumens. In some embodiments, the tubing assembly comprises a pair of tubes that are fused together. In some embodiments, the tubing assembly comprises three tubes that are fused together. In some embodiments, the tubing assembly comprises a plurality of tubes that are interconnected longitudinally by a coupling. In some embodiments, the coupling extends between a given pair of tubes of the plurality of tubes. In some embodiments, the plurality of tubes may be separated by tearing the coupling. In some embodiments, the tubing assembly comprises a pair of separate tubes. In some embodiments, at least one of the first adapter assembly and the second adapter assembly further comprises a tube identifier portion. In some embodiments, the tube identifier portion extends from one side of the first adapter assembly or the second adapter assembly such that the tube identifier portion is readable when the tubing and adapter assembly is installed in the peristaltic pump.

In another embodiment, a method of manufacturing a clamp-less tubing assembly for a peristaltic pump is disclosed. The method includes the steps of pressing a first pump tubing gripper into a first end of a tube; pressing a second pump tubing gripper into a second end of a tube; overmolding a first external system interface over the first pump tubing gripper and the first end of the tube; and overmolding a second external system interface over the second pump tubing gripper and the second end of the tube. In some embodiments, the method further includes the step of one of coupling a pump tubing interface to the external system interface and molding a pump tubing interface to said external system interface. In some embodiments, coupling the pump tubing interface to the external system interface further includes coupling the pump tubing interface to the external system interface using one of spin welding, sonic welding, adhesion, and threaded fastening. In some embodiments, the method further includes the step of providing a cap and inserting the cap into one of the first pump tubing gripper and the second pump tubing gripper.

In yet another embodiment, a peristaltic pump assembly is disclosed. The assembly includes a peristaltic pump having a cover with at least one magnifying portion and a tubing and adapter assembly configured for use with the peristaltic pump. The tubing and adapter assembly includes an elongate body defining a longitudinal axis, a first end, and a second end, the elongate body having a plurality of lumens extending along the longitudinal axis, each lumen being surrounded by a tube wall, the plurality of lumens extending from the first end to the second end such that the first end is in fluid communication with the second end of the elongate body, a first external system interface having an annular surface defining a first flow passage, a first tubing interface portion, a first pump interface portion, a first mounting interface portion, and a first tube identifier portion, the first external system interface molded over the first end of the elongate body, and a second external system interface having an annular surface defining a second flow passage, a second tubing interface portion, a second pump interface portion, a second mounting interface portion, and a second tube identifier portion, the second external system interface molded over the second end of the elongate body. The first and second tube identifier portions are viewable through the cover of the peristaltic pump and the at least one magnifying portion is configured to magnify at least one of the first and second tube identifier portions when viewed through the cover.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIG. 20A illustrates a peristaltic tubing assembly, according to another embodiment.

FIG. 20B illustrates an exploded view of the peristaltic tubing assembly of FIG. 20A.

FIG. 20C illustrates an enlarged view of the peristaltic tubing assembly shown in FIG. 20A.

FIG. 21A illustrates a peristaltic tubing assembly, according to another embodiment.

FIG. 21B illustrates an exploded view of the peristaltic tubing assembly of FIG. 21A.

FIG. 22A illustrates a peristaltic tubing assembly, according to another embodiment.

FIG. 22B illustrates an exploded view of the peristaltic tubing assembly of FIG. 22A.

FIGS. 23A-F illustrate views of a pump tubing gripper/lock for a peristaltic pump tubing assembly, according to an embodiment.

FIGS. 24A-F illustrate views of a pump tubing gripper/lock for a peristaltic pump tubing assembly, according to another embodiment.

FIGS. 28A-C illustrate views of an external system interface/adapter for a peristaltic pump tubing assembly, according to another embodiment.

FIGS. 29A-C illustrate views of an external system interface/adapter for a peristaltic pump tubing assembly, according to another embodiment.

FIGS. 30A-C illustrate views of an end fitting for a peristaltic pump tubing assembly, according to an embodiment.

FIGS. 31A-C illustrate views of an end fitting for a peristaltic pump tubing assembly, according to another embodiment.

FIGS. 32A-C illustrate views of an end fitting for a peristaltic pump tubing assembly, according to another embodiment.

FIG. 35 illustrates a peristaltic tubing assembly, according to another embodiment.

FIG. 39 illustrates a detailed view of a magnifying area of the peristaltic pump shown in FIG. 38.

DETAILED DESCRIPTION

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. In the description that follows, a peristaltic pump tubing assembly may include a tube or lumen. The terms "tube" and "lumen" are not synonymous. However, in the following description, the term "tube" is used generally to refer to peristaltic pump tubing which may also include one or more lumens.

As noted above, embodiments of the present inventions can overcome several prior art deficiencies and provide advantageous results. Some embodiments provide for a peristaltic pump that can operate at high pressures while maintaining a high flow rate. Some embodiments therefore allow the peristaltic pump to operate effectively at higher pressures and flow rates without requiring that the pump have a larger motor. Further, some embodiments can comprise a tubing assembly that can operate at high pressures and flow rates without requiring a larger wall thickness. Furthermore, some embodiments can comprise a tubing assembly that utilizes multiple lumens that are acted upon by one or more rollers to achieve a high flow rate at high pumping pressures. Some embodiments of tubing assemblies that utilize multiple lumens are discussed in U.S. patent application Ser. No. 13/011,822, entitled "HIGH PRESSURE, HIGH FLOW RATE TUBING ASSEMBLY FOR A POSITIVE DISPLACEMENT PUMP," filed Jan. 21, 2011, which is hereby incorporated by reference in its entirety.

Figure 1:
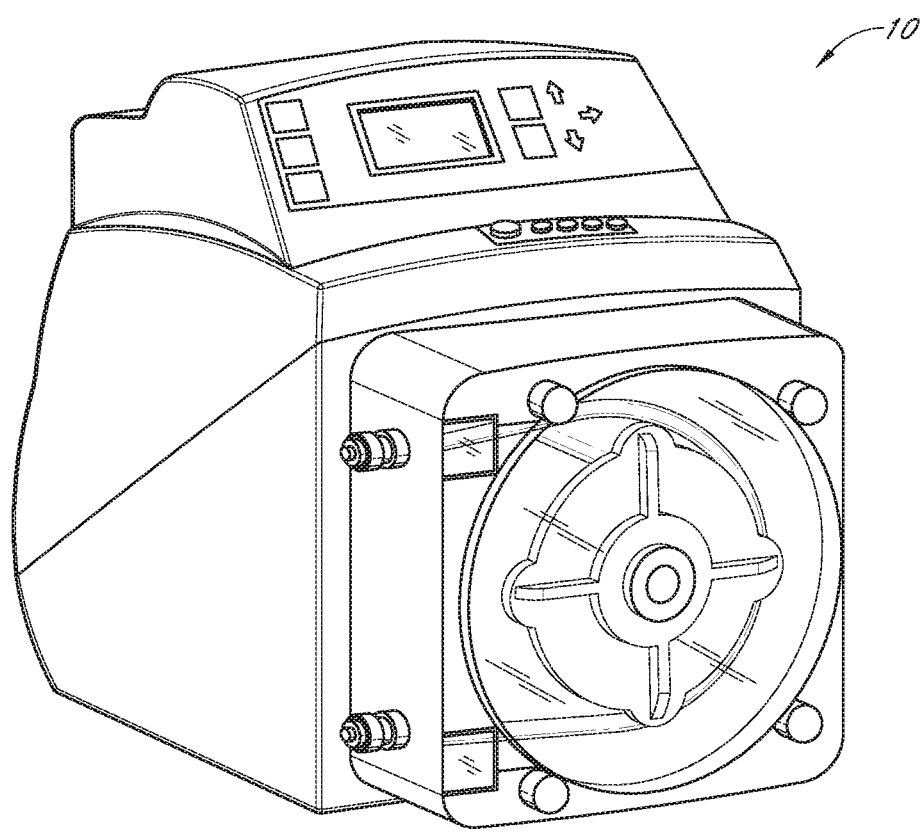
FIG. 1 is a perspective view of a prior art peristaltic pump.
Figure 2:
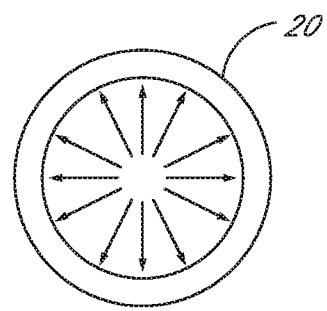
FIG. 2 is a cross-sectional view of tubing of the prior art peristaltic pump shown in FIG. 1.

FIG. 1 illustrates a prior art peristaltic pump 10 that uses a single tube 20, which is shown in cross-section in FIG. 2. As discussed above, one of the problems associated with a single tube arrangement in a peristaltic pump is that the pressure and flow rate are limited. For example, if the pressure is to be increased, the wall thickness of the tubing must also be increased, which creates additional stress on the pump drive. Further, if the flow rate is to be increased, the inner diameter of the tubing and/or the roller RPM must also be increased, which can result in shorter tubing life and higher stress on the pump drive. Therefore, in order to increase both the pressure and flow rate, the tubing life is generally decreased while tubing failure and pump stress is increased. Therefore, at least one of the embodiments disclosed herein reflects that an increased pressure and/or flow rate has only been possible by sacrificing tubing life or increasing the size of the motor of the peristaltic pump.

Figure 3:
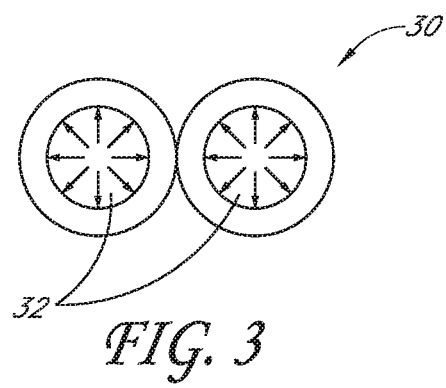
FIG. 3 is a cross-sectional view of a tubing assembly, according to an embodiment disclosed herein.
Figure 4:
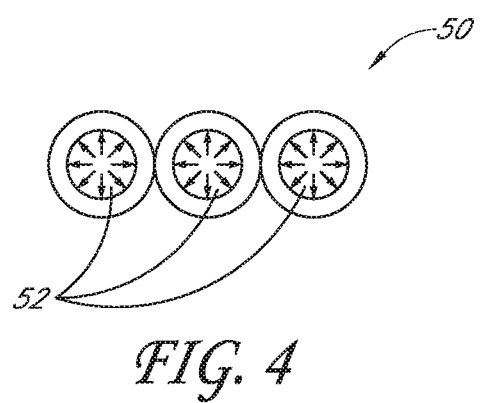
FIG. 4 is a cross-sectional view of a tubing assembly, according to another embodiment disclosed herein.

FIGS. 3-4 illustrate embodiments of a tubing assembly fabricated in accordance with principles of the inventions disclosed herein. For example, FIG. 3 illustrates a tubing assembly 30 having a pair of lumens 32. FIG. 4 similarly illustrates a tubing assembly 50 having a plurality of lumens 52. Further, the tubing assembly can be configured to comprise four or more lumens. Some additional embodiments of a tubing assembly fabricated in accordance with principles of the inventions disclosed herein are shown in FIGS. 22A-C. For example, FIG. 22A illustrates a tubing assembly 60 having a pair of lumens 62 separated by an attachment portion 64. FIG. 22B illustrates a tubing assembly 70 having a single lumen 72 according to the prior art. FIG. 22C illustrates a tubing assembly 80 having a plurality of lumens 82 fully enclosed within a single lumen 84. As shown in FIG. 22C, the inner lumens may be tangential with one another and with the inner diameter of the enclosing lumen.

The lumens of tubing assembly can extend along a longitudinal direction of the tubing assembly. In this regard, the tubing assembly can comprise a first end and a second end. The lumens of the tube assembly can extend intermediate the first end and the second end such that the first end and the second end are in fluid communication with each other.

Further, each of the lumens can be surrounded by a wall structure. In some embodiments, the lumens can be surrounded by a wall structure having a generally constant thickness. In other embodiments, the lumens can be surrounded by a wall structure having a variable thickness. However, in some embodiments, the wall thickness and inner diameter of the tube can be generally constant along the length of the tube.

Some embodiments reflect the realization that high pressures and high flow rates can be achieved in a peristaltic tube pump by using a system of one, two, or more small tubes. In some embodiments, multiple tubes can be used to replace a single tube in order to allow for pumping higher volumes at higher pressures. The tubes in such an arrangement can each be uniquely configured to provide desired strength and durometer characteristics. Through substantial testing and analysis, the Applicants have discovered excellent pressure, tube life, and flow characteristics using the measurements, ranges, and tubing characteristics disclosed herein.

For example, in some embodiments, the inside diameter of a tube can be within a range of at least about 1/16" (1.59 mm) and/or less than or equal to about 3" (76.2 mm). The inside diameter of a tube in some embodiments can be at least about 1/8" (3.18 mm) and/or less than or equal to about 1.5" (25.4 mm). Further, in some embodiments, the inside diameter of a tube can be at least about 1/2" (12.7 mm) and/or less than or equal to about 1" (25.4 mm). For some larger capacity applications, the inside diameter of a tube can be about 3/4" (19.1 mm). For some smaller capacity applications, the inside diameter of a tube can be about 3/8" (9.5 mm). In some embodiments, such as the embodiment illustrated in FIG. 22C, the inner diameter of a pair of lumens enclosed within a single outer lumen may be at least about 1/8" (3.18 mm) and/or less than or equal to about 1.5" (25.4 mm) and the inner diameter of the single outer lumen may be at least about 1/4" (6.36 mm) and/or less than or equal to about 3" (50.8 mm). Two or more tubes can be used together in a tubing application. Thus, a tubing assembly can be provided in which two or more tubes having an inside diameter within the ranges or at the dimensions listed above.

Further, embodiments are provided in which the tube wall thickness is within a range of at least about 1/32" (0.80 mm) and/or less than or equal to about 1" (25.4 mm). In some embodiments, the tube wall thickness can be within a range of at least about 1/16" (1.59 mm) and/or less than or equal to about 1/2" (12.7 mm). In some embodiments, the tube wall thickness can be within a range of at least about 1/8" (3.18 mm) and/or less than or equal to about 5/16" (7.94 mm). In some larger applications, the tube wall thickness can be about 9/32" (7.14 mm). In smaller applications, the tube wall thickness can be about 3/16" (4.76 mm).

Additionally, some embodiments reflect the realization that high pressures and high flow rates can be achieved in a peristaltic tube pump by using a system of one, two, or more tubes in which each tube has a specific relationship between the inner diameter, tube wall thickness, and/or the durometer of the tube. In embodiments using more than one tube, the tubes can be identical. However, the tubes can have different dimensions; for example, the tubes can vary in inner diameter, tube wall thickness, and/or tube durometer. Additionally, as the tube wall thickness increases, the horsepower of the motor must also increase.

In some embodiments, the tube can be configured to have a ratio of tube wall thickness to tubing inner diameter of at least about 20% (0.2:1) and/or less than or equal to about 125% (1.25:1). In some embodiments, the ratio of the tube wall thickness to the inside diameter of a tube can be at least about 20% (0.2:1) and/or less than or equal to about 60% (0.6:1). In some embodiments, the tube can be configured to have a ratio of tube wall thickness to tubing inner diameter of at least about 25% (0.25:1) and/or less than or equal to about 50% (0.50:1). In some embodiments, the ratio of the tube wall thickness to the inside diameter of a tube can be at least about 25% (0.25:1) and/or less than or equal to about 45% (0.45:1). Further, in some embodiments, the ratio of the tube wall thickness to the inside diameter of a tube can be at least about 27% (0.27:1) and/or less than or equal to about 43% (0.43:1). It has been found in some embodiments that excellent pumping qualities and results are achieved when the ratio of tube wall thickness to the inside diameter of a tube is about 28% (0.28:1).

For example, in some embodiments, the inside diameter of a tube can be at least about 1/16" (1.59 mm) and/or less than or equal to about 2" (50.8 mm), and the tube wall thickness of the tube can be at least about 1/32" (0.80 mm) and/or less than or equal to about 5/8" (15.9 mm). Further, in some embodiments, the inside diameter of a tube can be at least about 3/8" (9.53 mm) and/or less than or equal to about 1.5" (38.1 mm), and the tube wall thickness of the tube can be at least about 1/8" (3.175 mm) and/or less than or equal to about 1/2" (12.7 mm). In some larger applications, the inside diameter of a tube can be about 1" (25.4 mm), and the tube wall thickness of the tube can be about 5/16" (7.94 mm). In other applications, the inside diameter of a tube can be about 3/4" (19.1 mm), and the tube wall thickness of the tube can be about 7/32" (5.56 mm). One, two, three, four, or more tubes having such dimensions can be used in a peristaltic tube pump.

In some embodiments, the durometer of a tube can be within the Shore A hardness, within a range of at least about 70 and/or less than or equal to about 90. In some embodiments, the durometer of a tube can be at least about 75 and/or less than or equal to about 90. Further, the durometer of a tube can be at least about 80 and/or less than or equal to about 90. The durometer of a tube can be at least about 83 and/or less than or equal to about 90. Furthermore, the durometer of a tube can be at least about 85 and/or less than or equal to about 89. Durometer values within the above-noted ranges can be implemented for a tube having an inner diameter and/or thickness within any of the above-noted ranges for those parameters. For example, a tube can have inside diameter of at least about 1/16" (1.59 mm) and/or less than or equal to about 1/2" (12.7 mm), a tube wall thickness of at least about 3/32" (2.38 mm) and/or less than or equal to about 3/16" (4.76 mm), and a durometer of at least about 75 and/or less than or equal to about 90.

In their studies, Applicants have found excellent test results when comparing multi-tube tubing assemblies to single tube tubing assemblies having approximately equivalent flow rates. In particular, when compared to similar single tube tubing assemblies, multi-tube tubing assemblies provide a much higher tube life before tube failure and experience minimal variance or drop-off in flow rate during the life of the tube.

For example, Applicants have discovered that a dual tubing assembly having tubes with a 3/8" inside diameter, a durometer of 80, and a tube wall thickness of between about 0.095" to about 0.10", tested with water at 30 PSI and 125 RPM, resulted in tube life of 1072 hours until failure. At these dimensions, the ratios of the wall thickness to the inside diameter is about 26%. Further, at 30 PSI and 125 RPM, the dual tubing assembly had a flow rate drop of only 1.25% over the life of the tube (indicative of superior tubing memory characteristics). In particular, the flow rate at start-up was about 7580 ml/min and the flow rate about 24 hours prior to tube failure was 7485 ml/min.

In contrast, a single 1/2" inside diameter tube and a tube wall thickness of about 0.125", was tested with water at 30 PSI and 125 RPM and resulted in a tube life of only 344 hours until failure. Further, at 30 PSI and 125 RPM, the single tube had a flow rate drop of 21.4% over the life of the tube (indicative of poor tube memory characteristics). In particular, the flow rate at start-up was about 6900 ml/min and the flow rate about 24 hours prior to tube failure was about 5420 ml/min.

In further contrast, a single 3/4" inside diameter tube and a tube wall thickness of about 0.125", was tested with water at 30 PSI and 125 RPM and resulted in a tube life of only 270 hours until failure. Further, at 30 PSI and 125 RPM, the single tube had a flow rate drop of 19.1% over the life of the tube (indicative of poor tube memory characteristics). In particular, the flow rate at start-up was about 9043 ml/min and the flow rate about 24 hours prior to tube failure was about 7316 ml/min.

Accordingly, based on these results, embodiments of a multi-tube tubing assembly can provide far superior tube life and maintain higher flow rates with minimal flow rate reduction over the life of the tubing assembly when compared with a single, larger inside diameter tube that provides approximately the same flow rate as the multi-tube tubing assembly. In this regard, a tubing assembly of two 3/8" inside diameter tubes would provide higher tube life and lower variance than a comparable 9/16" inside diameter single tube assembly. Further, other benefits are achieved including decreased loads that enable the use of a smaller pump, easier handling, and increased longevity and efficiency in an operation. Applicants also note that in the field of high pressure, high flow rate pumping, the loss of viable tube life and decrease in flow rate are longstanding problems with single tube designs and have been unresolved until the introduction of embodiments disclosed herein.

In some embodiments, Applicants have also found that the use of a multi-tube tubing assembly achieves higher flow rates than single tube assemblies due to an increased tubing length. For example, a 3/8" inside diameter dual tube assembly can have a 18 1/8" length as compared to a 1/2" inside diameter or 3/4" diameter single tube assembly that has a 17 3/4" length. The 18 1/8" length of tubing advantageously provides improved flow rates as opposed to the 17 3/4" length.

Accordingly, some multi-tube embodiments can provide additional advantages over single tube assemblies.

A desirable ratio of tube wall thickness to the tube durometer can beneficially enable the tubing to have an optimal size and performance. Some embodiments can be configured such that the wall thickness of the tube can be inversely related the durometer of the tube. The thickness and durometer can be modified to provide various benefits, such as enabling the use of a pump motor that is much smaller and more efficient than the traditional counterpart pump required for a peristaltic hose pump. Moreover, some embodiments are capable of pumping at high pressures (exceeding 100 to 125 PSI) and high flow rates while also resulting in increased tube life, increased drive efficiency, lower replacement cost, lower energy consumption, cooler operating temperatures, reduced operating and maintenance costs, and reduced shipping costs.

The lumens of the tubing assembly can also be coupled or joined within the tubing assembly using a variety of manufacturing techniques. In some embodiments, the tubing assembly can be extruded and therefore comprise a monolithic part. Some embodiments can comprise two or more separate parts. For example, some embodiments can be configured such that the tubing assembly 30 comprises one or more tubes that are fused together at a joint. Such an embodiment is shown in FIGS. 3 and 4. Additionally, some embodiments can be configured such that the tubing assembly comprises a plurality of tubes that are coupled to each other via an intermediate coupling or attachment portion.

Moreover, some embodiments can be configured to comprise a plurality of individual tubes. For example, a plurality of individual tubes can be disposed side-by-side within the pump head or cavity of the peristaltic pump.

In addition, when the tubing assemblies of 30, 50 are compared to the tubing assembly 20, the volume capacity of the tubing assemblies 30, 50 can be the same as the tubing assembly 20. For example, the flow area or cross-sectional area as defined by the inner diameter of the lumens of the tubing assemblies 30, 50 can be equal to the flow area or cross-sectional area as defined by the inner diameter of the lumen of the tubing assembly 20. Other advantages may also be present which enable the volume capacity of the tubing assemblies to be equivalent as well.

For example, the rotations per minute (RPM) or drive speed of the roller assembly may be higher when the tubing assemblies 30, 50 are used because of the lower rolling resistance and loading on the pump motor. Thus, it is possible to use tubing assemblies having a flow area that is smaller than a comparable prior art tube while maintaining a common volume capacity or flow rate. Indeed, the volume capacity or flow rate of a given embodiment can be greater than the volume capacity or flow rate of a prior art tube that has a larger flow area than that of the given embodiment. An additional benefit of embodiments disclosed herein is that the volume capacity or flow rate of an embodiment can be equal to the volume capacity or flow rate of a prior art tube while reducing the load on the pump motor. In this manner, embodiments disclosed herein can advantageously increase tubing life and pump motor life.

Figure 5:
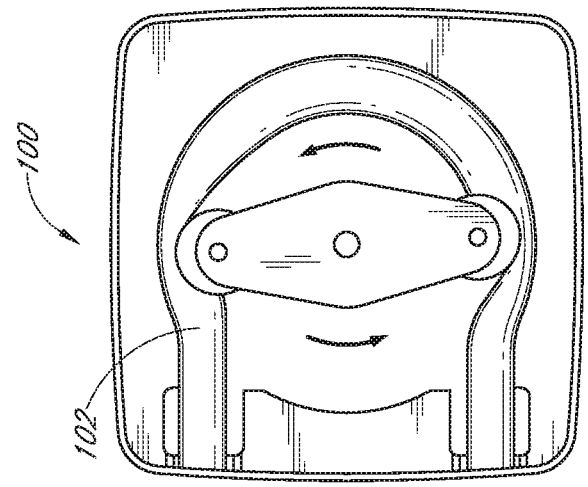
FIG. 5 illustrates the interaction of rollers in a peristaltic pump head when operating against prior art tubing.

FIG. 5 illustrates a prior art peristaltic pump 100 in which the tubing 102 is a larger size in order to provide for a higher flow rate. The rollers of the peristaltic pump operate against the tubing 102 and create a large depression in the tubing 102 as the tubing 102 is compressed against the interior wall of the pump head or pump cavity. As a result, the rollers encounter greater resistance and overall, the peristaltic pump is subjected to high loads with the tubing 102 being compressed and deformed against the roller.

Additionally, as the pump 100 operates at high pressures, the tubing 102 can be subject to significant internal pressures which can result in ballooning and/or rupture of the tubing 102. This unfortunate result is due at least in part to the wall thickness of the tubing 102 and the inner diameter of the tubing 102. Therefore, if the wall thickness of the tubing 102 is not increased, the tubing 102 may be subject to failure at high pressures. However, if the wall thickness of the tubing 102 is increased, the rollers of the pump will encounter a greater resistance in compressing the tubing 102 and therefore result in an increased load for the peristaltic pump 100.

Figure 6:
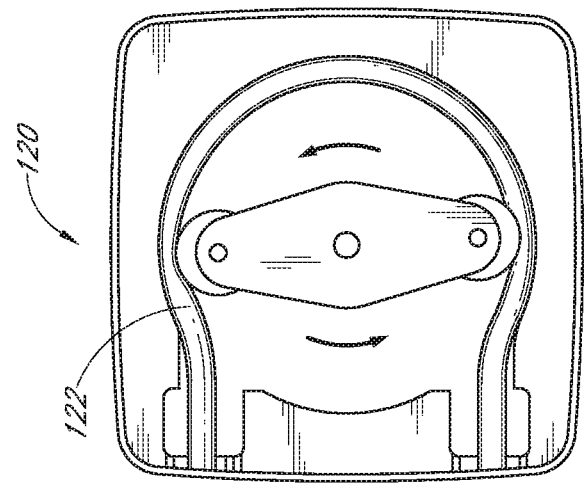
FIG. 6 illustrates the interaction of rollers in a peristaltic pump head when operating against a tubing assembly according to an embodiment disclosed herein.

FIG. 6 illustrates a peristaltic pump 120 and tubing 122 formed in accordance with an embodiment disclosed herein. Although shown in side view, the tubing 122 comprises a plurality of lumens, similar to one of the embodiments illustrated above in FIGS. 3-4. As will be discussed further herein, the tubing 122 can also be representative of another embodiment, such as one of the embodiments illustrated in FIGS. 7-14.

As shown, the tubing 122 is comparatively much smaller in outer diameter than the tubing 102 illustrated in FIG. 5. Thus, the tubing 122 can be configured to provide an appropriate wall thickness to inner diameter ratio while having a compression radius that is much smaller than the compression radius of the tubing 102. A "compression radius" can be considered as the amount of radial deflection of the tubing as measured relative to the axis of rotation of the roller assembly of the pump. The compression radius of the tubing 102 is illustrated as being much less than the compression radius of the tubing 122. Such a factor is relevant in computing rolling resistance of the roller assembly of the pump, which relates to the load on the pump in order to cause rotation of the roller assembly. Accordingly, when compared with the pump 100 and the tubing 102, the rollers of the peristaltic pump 120 will generally undergo a lower degree of rolling resistance while compressing against the tubing 122, thus decreasing the load on the pump 120.

Figure 7:
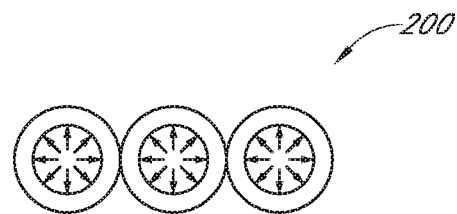
FIGS. 7-14 illustrate cross-sectional views of various tubing assemblies, according to embodiments disclosed herein.

FIGS. 7-14 illustrate various embodiments of tubing assemblies formed in accordance with the principles and teachings herein. FIG. 7 illustrates a tubing assembly 200 similar to the tubing assembly shown in FIG. 3.

Figure 8:
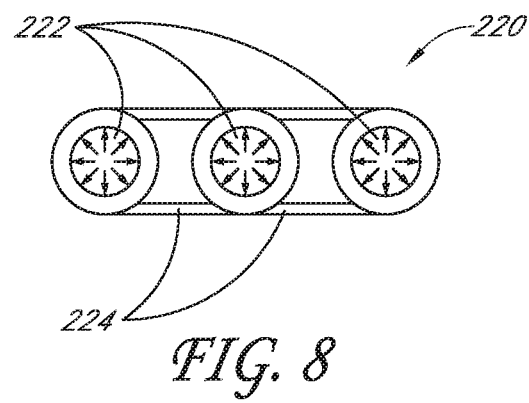

FIG. 8 illustrates a tubing assembly 220 having a plurality of lumens 222 through which fluid can pass. The tubing assembly 220 of FIG. 8 can be configured such that the lumens 222 are spaced apart from each other by a void, hollow portion, or lumen. The lumens 222 can each be disposed in a tube that is separated from an adjacent to by the void or lumen. The tubes can be interconnected via one or more couplings or attachment portions 224. The couplings or attachment portions 224 can extend along the entire length of the tubing assembly 220. Alternatively, the couplings or attachment portions 224 can have a longitudinal length that is less than the longitudinal length of the tubing assembly 220. In such an embodiment, the couplings or attachment portions 224 can be disposed at a plurality of longitudinal positions along the length of the tubing assembly 220.

Further, the couplings or attachment portions 224 can be separate from and later attached to the tubes or formed monolithically with the tubes in an extrusion process. For example, the middle tube of the tubing assembly 220 can be formed monolithically with the couplings or attachment portions 224 such that the overall thickness or width of the tubing assembly 220 as measured at the middle tube thereof does not exceed the outer diameter of the middle tube thereof.

Furthermore, the couplings or attachment portions 224 can extend generally tangentially relative to the tubes of the tubing assembly so as to connect upper and lower points of the tubes to each other. The dimension and the coupling of the couplings or attachment portions 224 can therefore be accomplished along the entire length of the assembly, along only a portion of the length of the tubing assembly, at one or more locations or positions along the tubing assembly, and/or integrated with one or more tubes of the tubing assembly. In this manner, the tubing assembly can therefore be configured generally in the shape of a ribbon of tubes.

Figure 9:
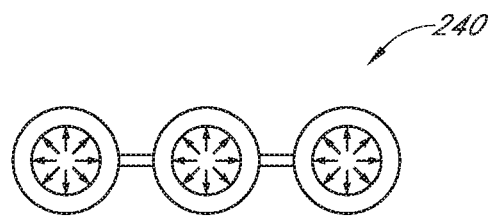

FIG. 9 illustrates a tubing assembly 240 having a plurality of tubes defining interior lumens. The tubes of the tubing assembly 240 can be coupled to each other by one or more couplings or attachment portions that extend intermediate the tubes. In particular, FIG. 9 illustrates that a single length of a coupling or attachment portion extends between a given pair of tubes. As noted above, the longitudinal dimension or length of the couplings or attachment portions can be equal to the longitudinal length of the tubing assembly or less than a longitudinal length of the tubing assembly. Further, in some embodiments, the couplings or attachment portions can be disposed at one or more positions along the length of the tubing assembly. FIG. 22C illustrates a similar tubing assembly 60 as that shown in FIG. 9. The tubes of the tubing assembly 60 can be coupled to each other by one or more couplings or attachment portions that extend intermediate the tubes. As discussed above, the coupling or attachment portion 64 that extends intermediate the tubes 62 of the tubing assembly 60 may be cut or severed along the longitudinal or length dimension of the attachment portion such that the tubes 62 may be separated lengthwise from each other.

Figure 10:
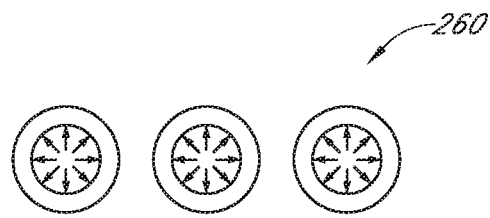
Figure 11:
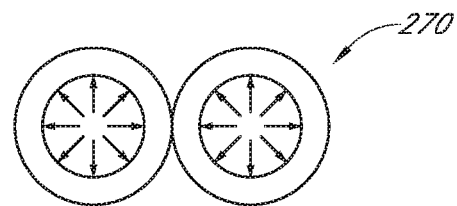
Figure 12:
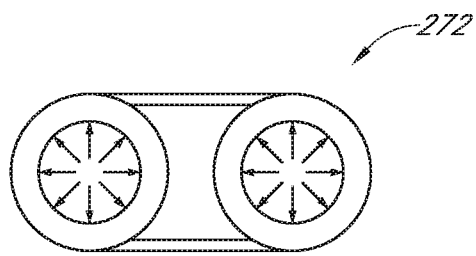
Figure 13:
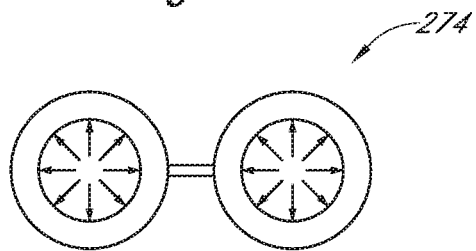
Figure 14:
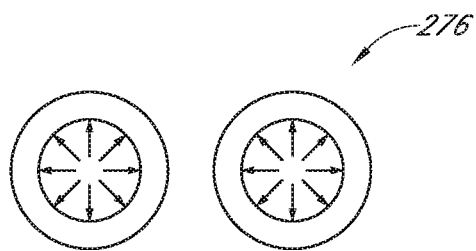

FIG. 10 illustrates a tubing assembly 260 comprising a plurality of tubes that each defines an interior lumen. In this embodiment, the tubes can be generally unconstrained or detached from each other. In particular, the tubing assembly can be devoid of any interconnections between the tubes. As such, the tubes can flex during compression without being physically constrained relative to each other.

As discussed above, each of the tubes of a tubing assembly can define a wall thickness. The wall thickness of a given tube can be different from the wall thickness of another tube of the tubing assembly. For example, one or more of the tubes of a tubing assembly can have an inner diameter, outer diameter, and/or wall thickness that is different from another of the tubes of the tubing assembly.

In addition, in embodiments that utilize a coupling or attachment portion, the ratio of the thicknesses of the coupling or attachment portion relative to the wall of the tube can be at least about 1:1 and/or less than or equal to about 1:3. In some embodiments, the ratio of the thicknesses can be about 1:2.

FIGS. 11-14 illustrate two-tube embodiments corresponding to the three-tube embodiments illustrated and discussed above in FIGS. 7-10. As shown, the embodiments in FIGS. 11-14 include a pair of tubes or lumens instead of three tubes or lumens. Nevertheless, the principles and features discussed above with respect to the tubing assemblies 200, 220, 240, 260 shown in FIGS. 7-10, as well as the tubing assemblies 60, 70, and 80 of FIGS. 22A-C, can also be applied to the embodiments of the tubing assemblies 270, 272, 274, and 276 shown in FIGS. 11-14. Accordingly, the above discussion is incorporated herein with respect to FIGS. 11-14, but will not be repeated. In accordance with the embodiments disclosed herein, a high flow rate can be obtained at high pressure.

Figure 15:
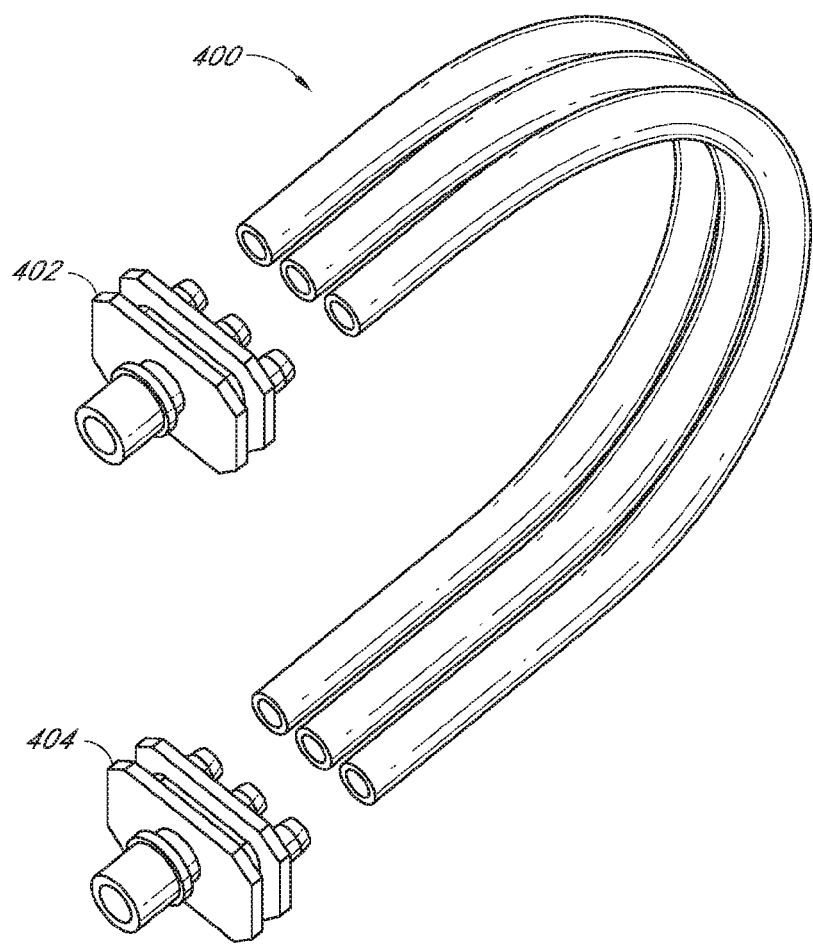
FIG. 15 illustrates a tubing assembly and connectors for a peristaltic pump, according to an embodiment.

FIG. 15 illustrates a tubing assembly 400 that can be coupled with first and second tubing connectors 402, 404. Once the tubing assembly 400 is coupled to the first and second tubing connectors 402, 404, the tubing assembly 400 can be installed into a peristaltic pump. Although the tubing assembly 400 is illustrated as comprising three lumens or tubes, the assembly 400 can comprise two, four, or more lumens or tubes. Further, the assembly 400 illustrates the use of a single inlet and a single outlet. Thus, in some embodiments, a single inlet and single fluid source can be split into a plurality of lumens or tubes in a tubing assembly, pumped through the pump head, and then rejoined through a single outlet. However, as shown in subsequent FIGS. 16-17 below, multiple pump sources can be used to feed lumens or tubes of a tubing assembly.

Figure 16:
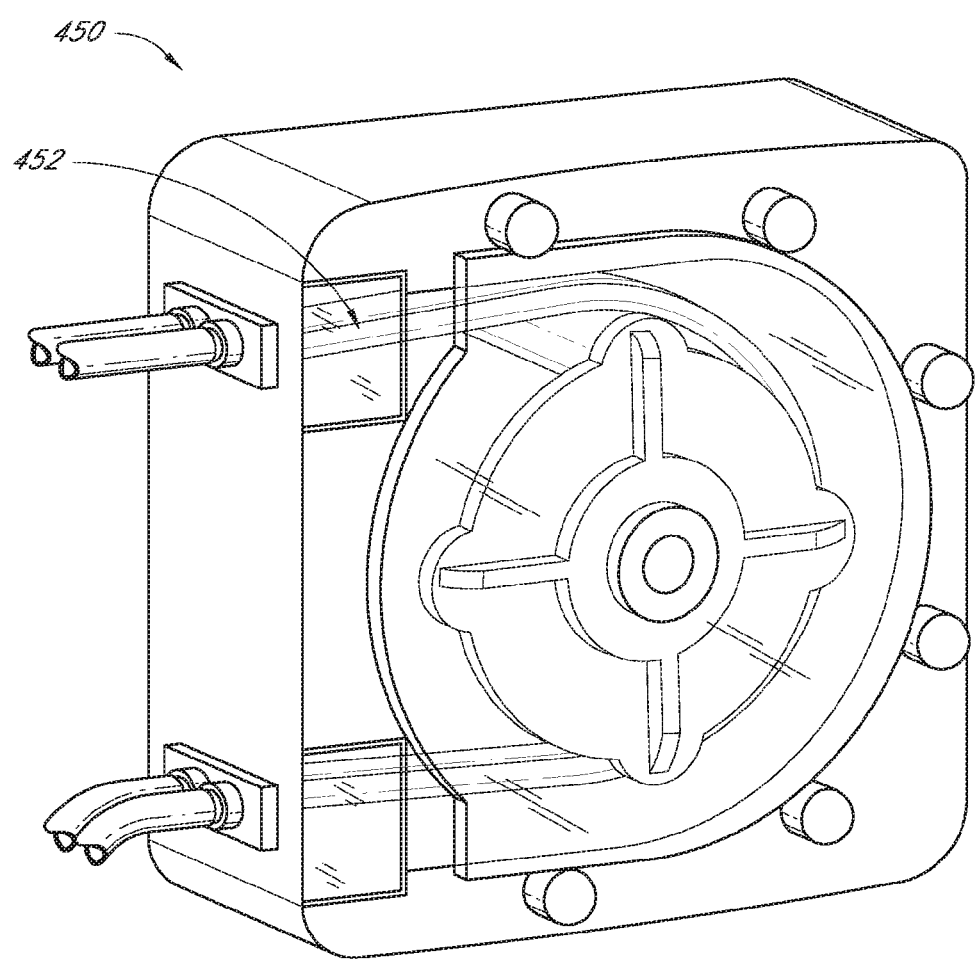
FIG. 16 illustrates a peristaltic pump having a tubing assembly formed in accordance with the principles disclosed herein, according to an embodiment.
Figure 17:
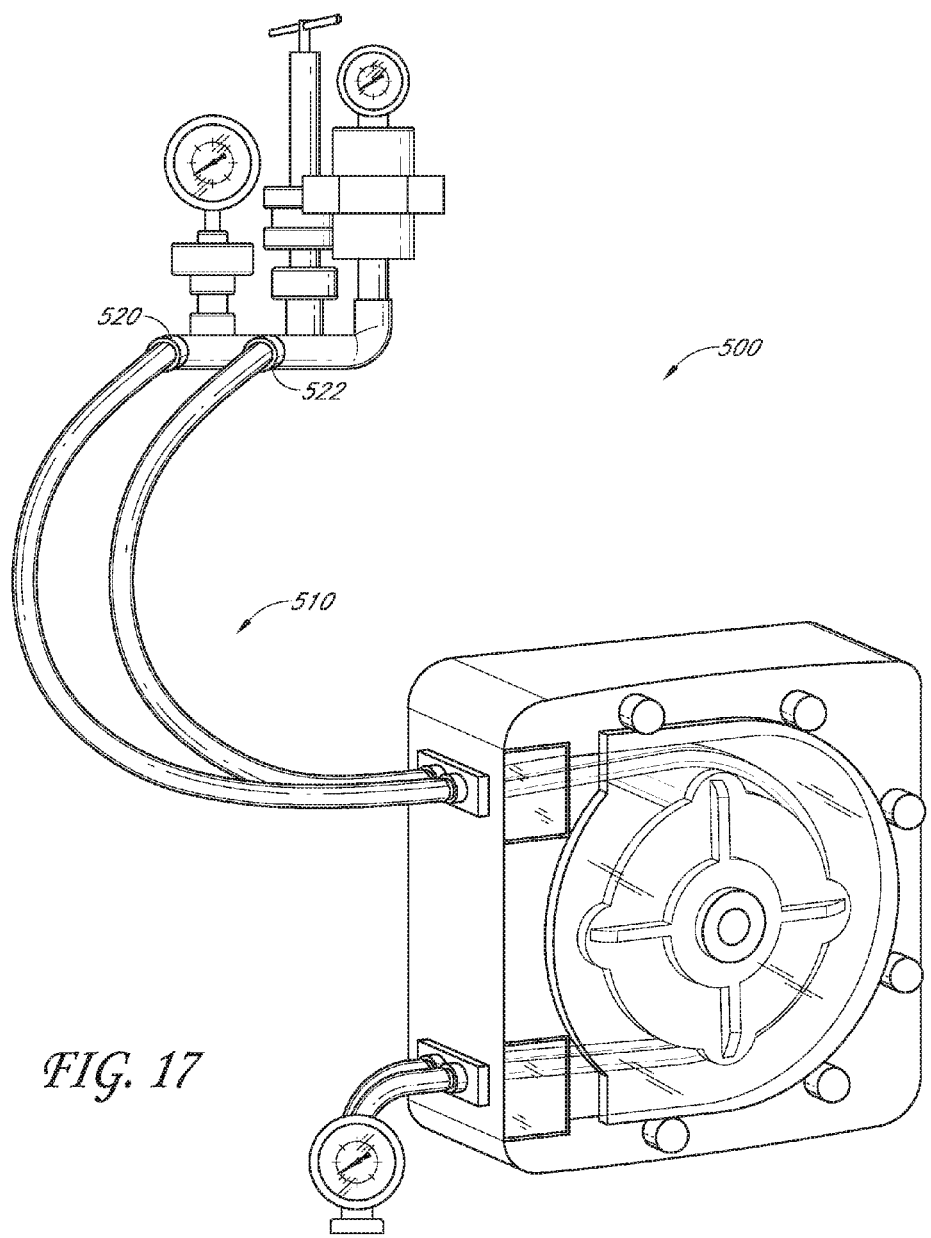
FIG. 17 illustrates a peristaltic pump and tubing assembly in accordance with an embodiment.

FIGS. 16-17 illustrate peristaltic pumps that utilize a tubing assembly according to an embodiment disclosed herein. As shown in FIG. 16, the peristaltic pump 450 can be retrofitted with a tubing assembly 452 of one of the embodiments disclosed herein without modifying the pump head or rollers. Thus, existing peristaltic pumps can beneficially use embodiments of the tubing assembly disclosed herein. However, the peristaltic pump can also be modified such that the pump cavity is deeper or wider in order to receive an embodiment of the tubing assembly's disclosed herein.

The tubing assembly of embodiments disclosed herein can comprise a plurality of lumens or tubes that are operatively connected to one or more fluid inlets and one or more fluid outlets. In this regard, as shown in FIG. 15, a plurality of tubes or lumens can be operatively connected to a single inlet and a single outlet. However, in some embodiments, as illustrated in FIG. 17, a peristaltic pump 500 can operate on a tubing assembly 510 in which an inlet of one or more of the tubes or lumens of the tubing assembly 510 is coupled to a first fluid source 520 and an inlet of another one or more tubes or lumens of the tubing assembly 510 is coupled to a second fluid source 522. Thus, the tubing assembly 510 can operate with one or more working fluids passing through one or more tubes or lumens thereof. The multiple fluid sources can be joined to a single outlet; however, multiple outlets can also be used that correspond to the multiple inlets and the fluids can be maintained separate.

Figure 18:
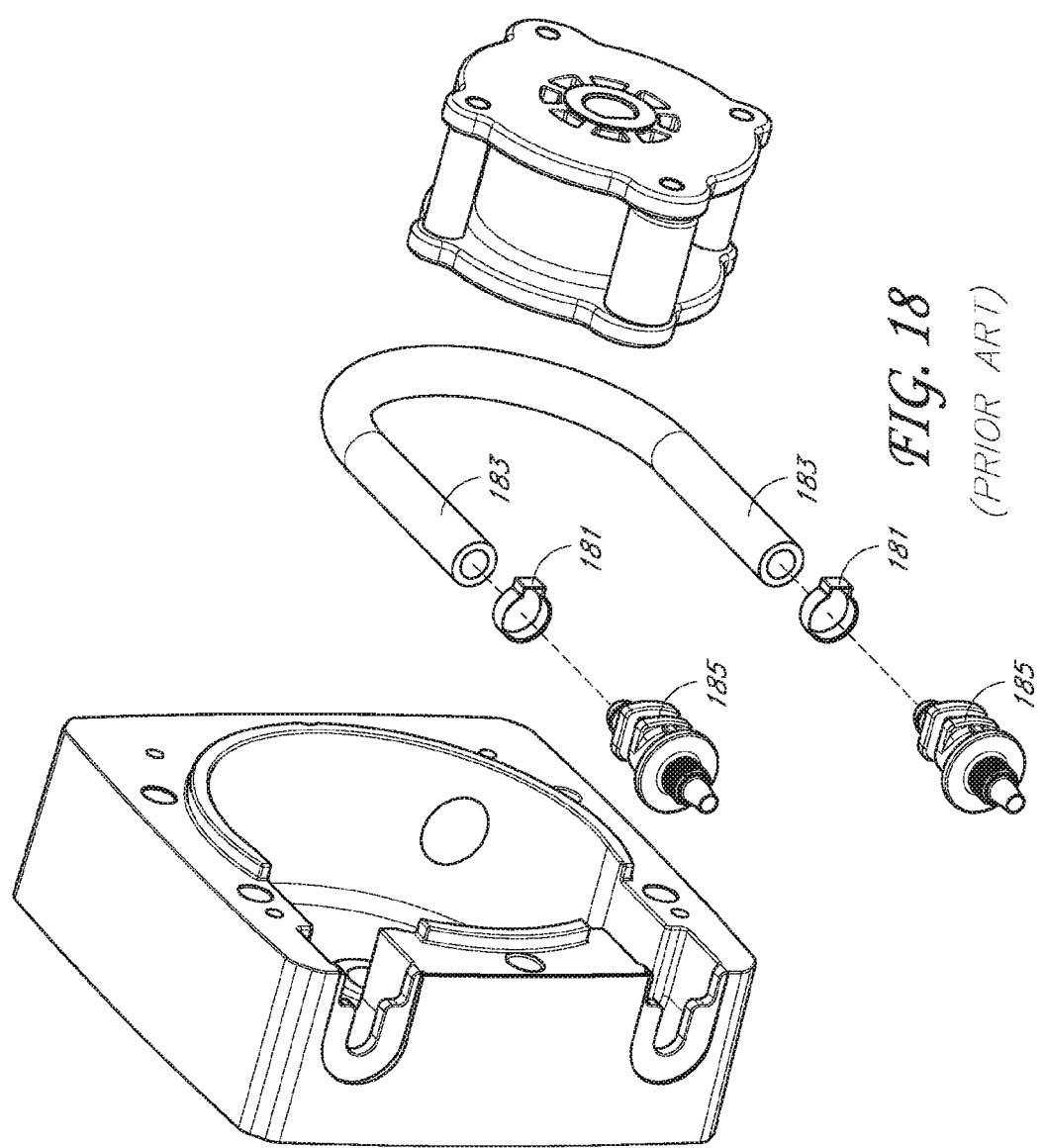
FIG. 18 illustrates a prior art peristaltic pump and tubing assembly.
Figure 19:
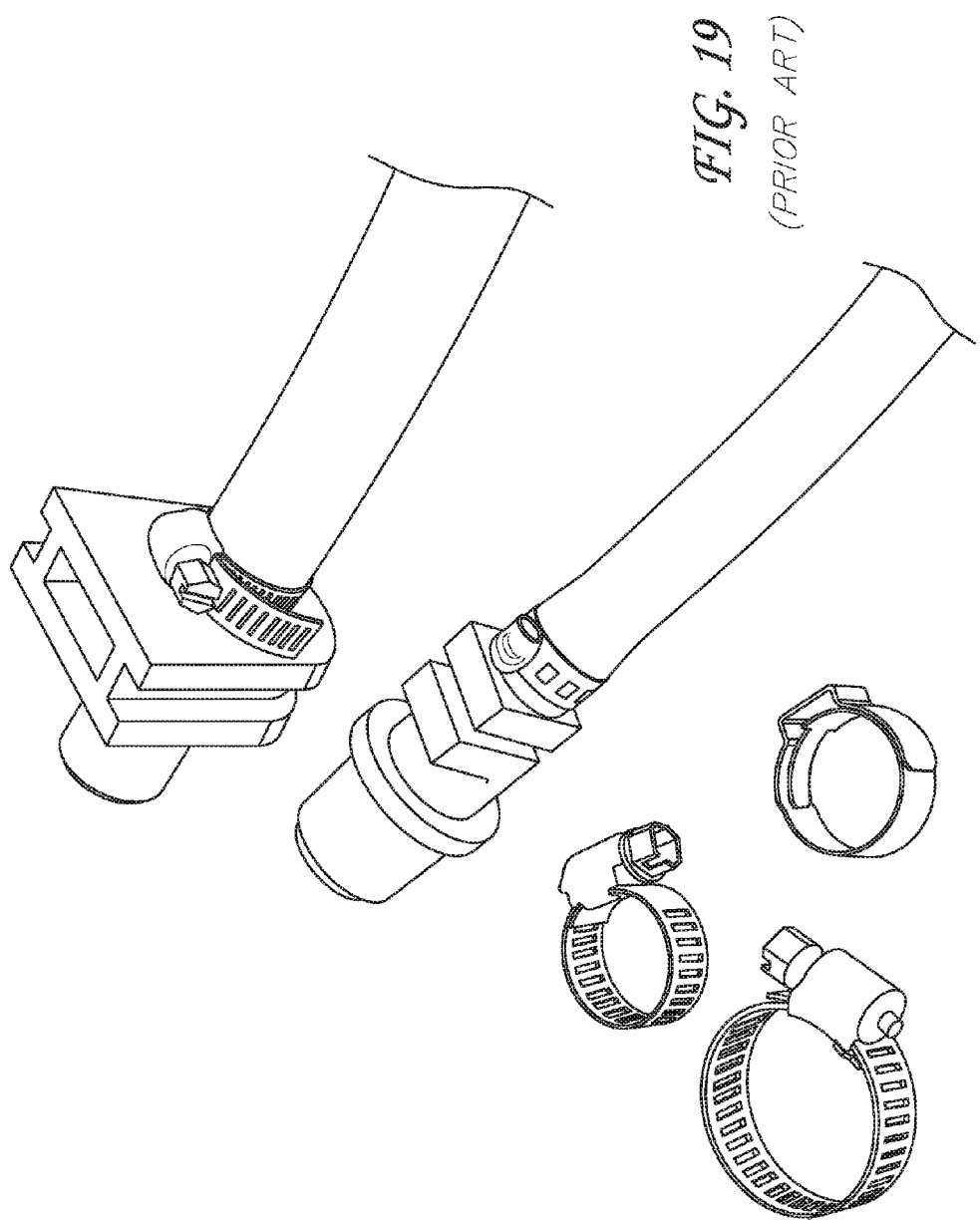
FIG. 19 illustrates a prior art tubing, clamp, and adapter assembly.
Figure 25A:
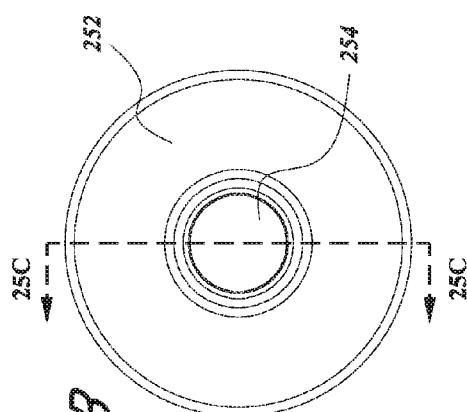
FIGS. 25A-D illustrate views of a cap for a peristaltic pump tubing assembly, according to an embodiment.
Figure 25B:
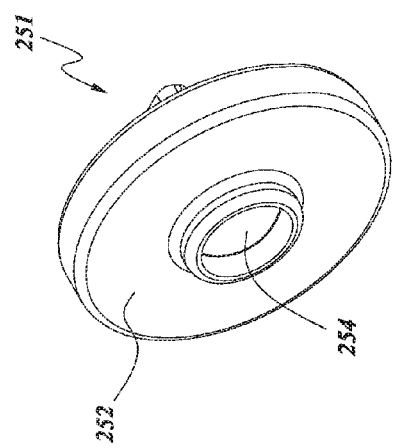
Figure 25C:
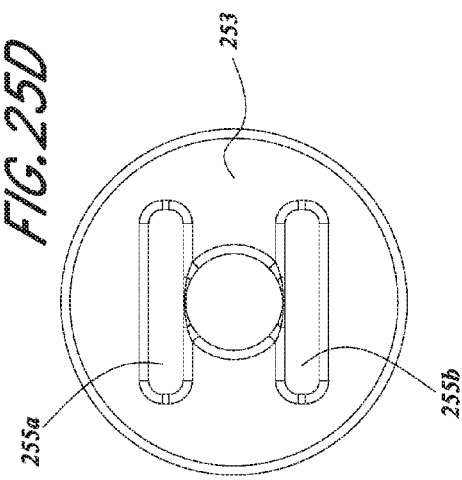
Figure 25D:
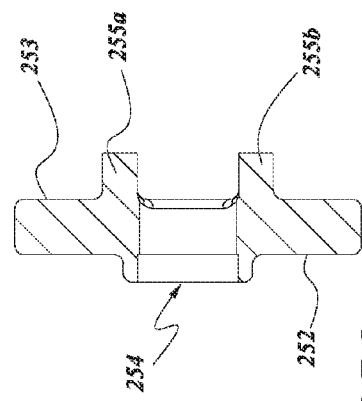

A prior art peristaltic pump and tubing assembly that uses clamps to secure the tubing to the adapter is shown in FIGS. 18 and 19. As shown, a metal tube clamp 181 is used to secure the tubing 183 to an adapter 185 which is then secured in the pump head housing. This type of tubing assembly is well known and does not generally require high tolerances between the hose barb and clamp-type adapter since the metal hose clamp 181 is adjustable, as shown most clearly in FIG. 19.

However, tubing assemblies configured with metal tube clamps have several disadvantages. Specifically, removal of the metal tube clamp removes a source of metal from the assembly. When assembled within a peristaltic pump, the tubing assembly is desirably leak-tight. However, should any part of the tubing assembly rupture or leak or chemical fumes enter the peristaltic pump housing, any metal pieces, such as the tube clamp, may corrode. Furthermore, tubing assemblies having tube clamps are bulky and the clamps take up space within the peristaltic pump housing. These space considerations are particularly important for multi-tube or multi-lumen tubing assemblies. Since each tube will require a separate tube clamp to secure the tubing to the hose barb, a multi-lumen assembly will include several bulky tube clamps taking up space within the peristaltic pump housing. A clamp-less assembly reduces the space occupied by the tubing and adapter assembly, particularly for a multiple tube assembly. In some embodiments, a clamp-less assembly reduces the space between the tubes of a peristaltic pump tubing assembly by at least 20%, at least 25%, at least 30%, at least 40%, at least 50% or at least 60%.

Furthermore, a large inventory of tubing assembly adapters is often stored to connect the tubing within the peristaltic pump to inlet and outlet tubes to meet customer requirements. As will be discussed in greater detail below, one embodiment illustrates an adapter system having interchangeable components that can be used to fit a variety of tubing profiles, such as single or dual tubes, and customer requirements, such as sanitary fittings, quick-connect fittings, etc. In some such embodiments, a smaller amount of inventory may be needed to satisfy customer requirements, thereby reducing inventory cost and improving inventory control.

In some embodiments, fluid leaks around the tube fittings may be minimized by overmolding the tube fittings to each end of the tubing. Overmolding is a process of combining two or more molded plastic or elastomer parts to make a single finished product. In one embodiment, the partially-assembled tubing assembly is placed within a mold and then additional plastic layer(s) are molded over and around the original part to form an overmolded adapter/external system interface that minimizes fluid leaks from around the tube fittings and the connection between the adapter/external system interface and the tubing.

FIGS. 20A, B, and C illustrate a clamp-less tubing assembly for a peristaltic pump, according to one embodiment. An overmolded peristaltic pump tubing assembly 201 is shown. As illustrated, the tubing 202 may be a multiple lumen tubing that defines two parallel flow paths similar to the tubing described above. In other embodiments, the tubing 202 may be single lumen tubing or may have two, three or more lumens. The tubing 202 has a first end and a second end. A first pump tubing gripper/lock 203a may be inserted into the first end of the tubing 202. A second pump tubing gripper/lock 203b may be inserted into the opposite or second end of the tubing 202. In some embodiments, a cap 204a fits within a recessed area in the pump tubing gripper/lock 203a. Similarly, a second cap 204b may be inserted within a recessed area within the second pump tubing gripper/lock 203b. As will be discussed in greater detail below, the tubing 202 with tubing grippers 203a, 203b and caps 204a, 204b may be inserted into a mold. Adapter/external system interfaces 206a, 206b may then be overmolded onto the tubing assembly to form an integrated tubing assembly. As will be discussed in greater detail below, the caps 204a, 204b may be used to stabilize the tubing assembly during the overmolding process. The external system interfaces 206a, 206b may be any type of external system interface used to connect the tubing of a peristaltic pump to the fitting of an inlet or outlet tube, such as hose barb, threaded, sanitary, quick-release connection, etc. as will be discussed in greater detail below. In some embodiments, the external system interfaces 206a, 206b overmolded to the tubing of a peristaltic pump may be the same or different external system interfaces, depending on customer requirements. In some embodiments, the overmolded external system interfaces may include end fittings, as illustrated by external system interfaces 206a, 206b. In other embodiments, as will be discussed below, end fittings may be spin welded or otherwise attached to the external system interfaces after the overmolding process. FIG. 20B illustrates that end fittings 208a, 208b may be spin welded or otherwise attached to the external system interfaces 206a, 206b after the overmolding process. In some embodiments, the end fittings 208a, 208b may be the same or different, depending on user requirements.

FIGS. 21A and B illustrate another embodiment of a clamp-less tubing assembly for a peristaltic pump, according to another embodiment. Similar to the overmolded peristaltic pump tubing assembly 201 shown in FIGS. 20A, B, and C, the overmolded peristaltic pump tubing assembly 211 comprises a multiple lumen tubing 212 that defines two parallel flow paths similar to the multiple lumen tubing described above. In other embodiments, the tubing 212 may be single lumen tubing or may have two, three or more lumens. The tubing 212 has a first end and a second end. A first pump tubing gripper/lock 213a may be inserted into the first end of the tubing 212. A second pump tubing gripper/lock 213b may be inserted into the opposite or second end of the tubing 212. As shown, the pump tubing gripper/locks 213a, 213b have two prongs or barbs that fit within the ends of the tubing 212. In other embodiments where the tubing has only one lumen, the pump tubing gripper/locks 213a, 213b will have one barb. In some embodiments, the number of barbs on the pump tubing gripper/locks 213a, 213b may equal the number of lumens of the tubing 212. As in the embodiment shown in FIG. 20B, a cap 214a fits within the pump tubing gripper/lock 213a. A second cap 214b similarly fits within the pump tubing gripper lock 213b. As will be discussed in greater detail below, the tubing 212 with tubing grippers 213a, 213b and caps 214a, 214b may be inserted into a mold. Adapter/external system interfaces 216a, 216b may then be overmolded onto the tubing assembly to form an integrated tubing assembly. As will be discussed in greater detail below, the caps 214a, 214b may be used to stabilize and maintain the diameter of the pump tubing gripper/lock 213a, 213b during the overmolding process. The external system interfaces 216a, 216b may be any type of external system interface used to connect the tubing of a peristaltic pump to the fitting of an inlet or outlet tube, such as hose barb, threaded, sanitary, quick-release connection, etc. as will be discussed in greater detail below. In some embodiments, the external system interfaces 216a, 216b overmolded to the tubing of a peristaltic pump may be the same or different external system interfaces, depending on customer requirements. FIG. 21B illustrates that end fittings 218a, 218b may be spin welded or otherwise attached to the external system interfaces 216a, 216b after the overmolding process. In some embodiments, the end fittings 218a, 218b may be the same or different, depending on user requirements.

Another embodiment of a clamp-less tubing assembly for a peristaltic pump is shown in FIGS. 22A and B. Similar to the overmolded peristaltic pump tubing assemblies 201 and 211 shown in FIGS. 20A and B and FIGS. 21A and B, the overmolded peristaltic pump tubing assembly 221 comprises a multiple lumen tubing 222 that defines two parallel flow paths similar to the multiple lumen tubing described above. In other embodiments, the tubing 222 may be single lumen tubing or may have two, three or more lumens. The tubing 222 has a first end and a second end. A first pump tubing gripper/lock 223a may be inserted into the first end of the tubing 222. A second pump tubing gripper/lock 223b may be inserted into the opposite or second end of the tubing 222. As shown, the pump tubing gripper/locks 223a, 223b have two prongs or barbs that fit within the ends of the tubing 222. In other embodiments where the tubing has only one lumen, the pump tubing gripper/locks 223a, 223b will have one barb. In some embodiments, the number of barbs on the pump tubing gripper/locks 223a, 223b may equal the number of lumens of the tubing 222. As in the embodiment shown in FIGS. 20B and 21B, a cap 224a fits within the pump tubing gripper/lock 223a. A second cap 224b similarly fits within the pump tubing gripper lock 223b. As will be discussed in greater detail below, the tubing 222 with tubing grippers 223a, 223b and caps 224a, 224b may be inserted into a mold. Adapter/external system interfaces 226a, 226b may then be overmolded onto the tubing assembly to form an integrated tubing assembly. As discussed above and as will be discussed in greater detail below, the caps 224a, 224b may be used to stabilize the tubing assembly during the overmolding process. The external system interfaces 226a, 226b may be any type of external system interface used to connect the tubing of a peristaltic pump to the fitting of an inlet or outlet tube, such as hose barb, threaded, sanitary, quick-release connection, etc. as will be discussed in greater detail below. In some embodiments, the external system interfaces 226a, 226b overmolded to the tubing of a peristaltic pump may be the same or different external system interfaces, depending on customer requirements. FIG. 22B illustrates that end fittings 228a, 228b may be attached to the external system interfaces 226a, 226b by spin welding, sonic welding, adhesion using glue or other adhesive, threaded connection, or mechanical fastening such as screws, nails, bolts, etc. after the overmolding process. In some embodiments, the end fittings 228a, 228b may be the same or different, depending on user requirements.

Figure 26B:
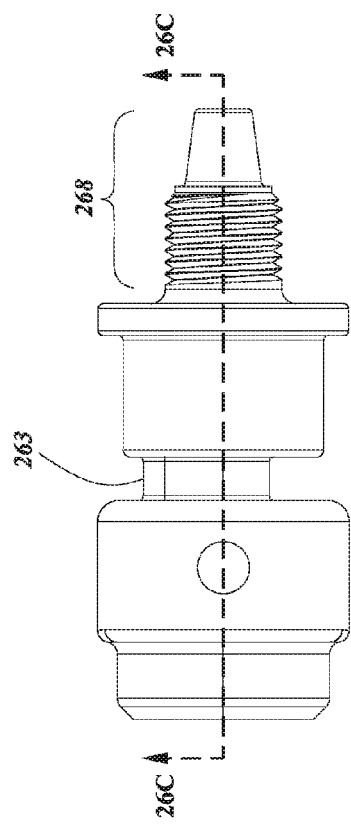
FIGS. 26A-C illustrate views of an external system interface/adapter for a peristaltic pump tubing assembly, according to an embodiment.
Figure 26C:
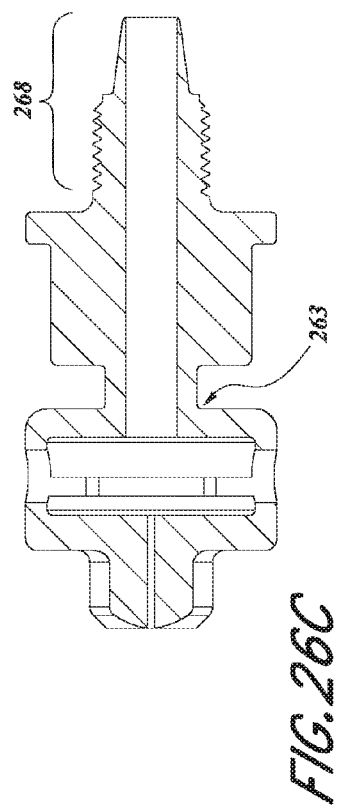
Figure 26A:
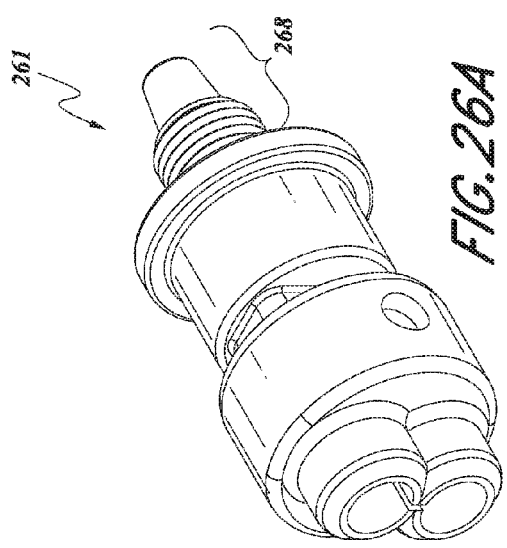
Figure 27B:
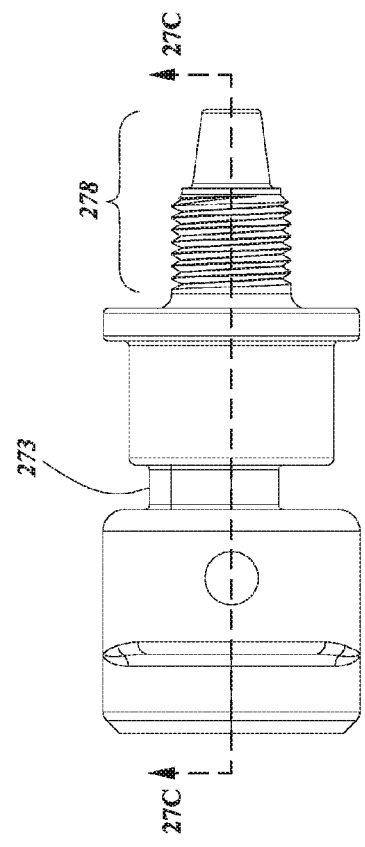
FIGS. 27A-C illustrate views of an external system interface/adapter for a peristaltic pump tubing assembly, according to another embodiment.
Figure 27A:
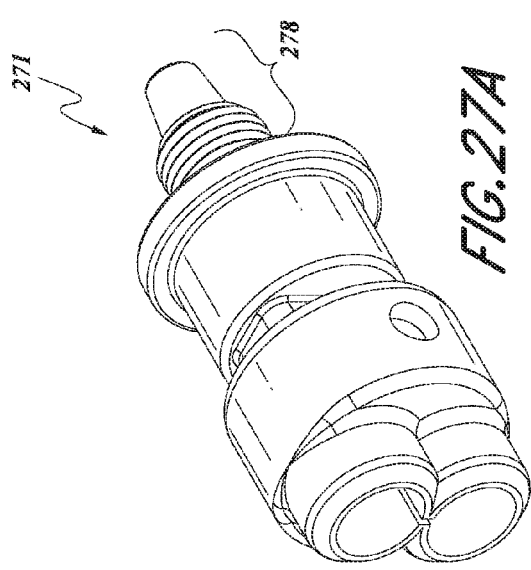
Figure 27C:
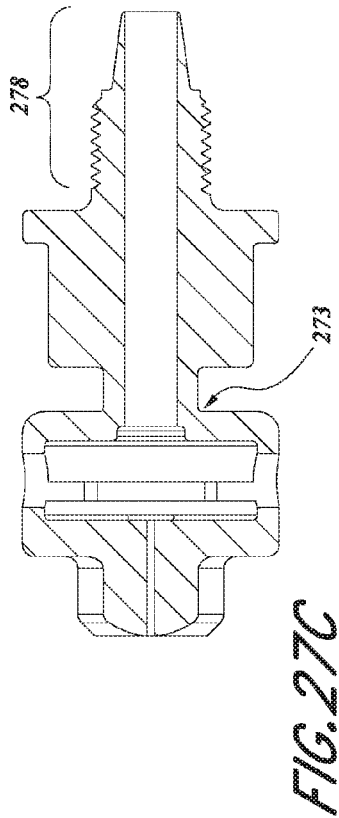
Figure 33B:
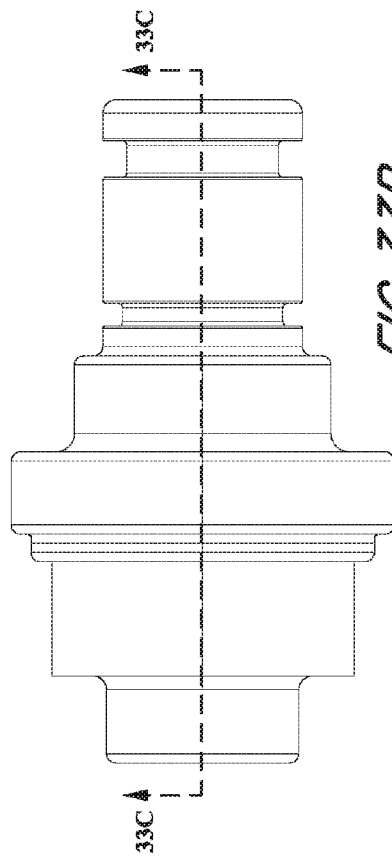
FIGS. 33A-C illustrate views of an end fitting for a peristaltic pump tubing assembly, according to another embodiment.
Figure 33C:
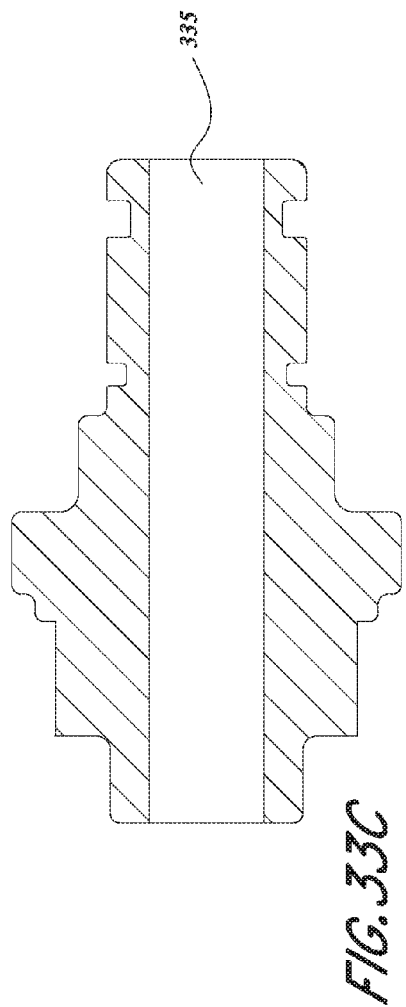
Figure 33A:
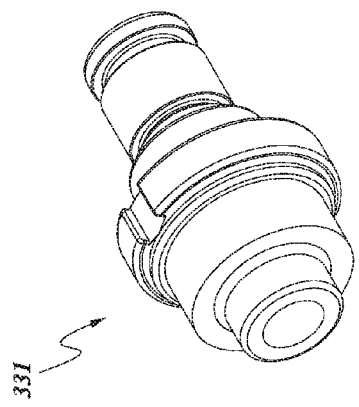

Several examples of an external system interface may be seen in FIGS. 26-33. FIGS. 26 and 27 illustrate adapter/external system interfaces 261 and 271 for dual lumen tubing as illustrated in FIGS. 20A-B, 21A-B, and 22A-B. Generally, in some embodiments, the external system interface is a hollow member that may be extruded, molded, or otherwise formed with a cylindrical passage extending the length of the external system interface. In some embodiments, such as those shown in FIGS. 26 and 27, a single fluid entrance may be split into two or more fluid exit chambers, depending on the number of lumens of the tubing being connected to the adapter/external system interface 261, 271. Referring to FIGS. 26 and 27, in some embodiments, each external system interface 261, 271 may include a tubing interface portion 268, 278 configured to connect with a corresponding interface on an inlet or outlet tube of the peristaltic pump, such as a tube supplying fluid to be pumped and a tube delivering the pumped fluid to another application. The adapter/external system interfaces 206a, 206b shown in FIG. 20B also illustrate a tubing interface portions 208a, 208b configured to connect with a corresponding interface on an inlet or outlet tube of the peristaltic pump.

In some embodiments, the overmolded external system interface may not include an end fitting or tubing interface portion configured to connect with a corresponding interface on an inlet or outlet tube of a peristaltic pump. FIGS. 28 and 29 illustrate external system interfaces 281 and 291 having a flange 282, 292 configured to connect to end fittings or tubing interface portion such as those shown in FIGS. 30-33 and discussed in greater detail below. The flanges 282, 292 allow the tubing interface portions to be spin welded or otherwise attached to the external system interfaces 281, 291 such that an inlet or outlet tube of a peristaltic pump, such as a tube supplying fluid to be pumped and a tube delivering the pumped fluid to another application may be attached to the overmolded tubing assembly. Examples of this assembly are shown in FIGS. 21B and 22B. Tubing interface portions 218a, 218b and 228a, 228b may be attached to the external system interfaces 216a, 216b and 226a, 226b, respectively, by spin welding, sonic welding, adhesion using glue or other adhesive, threaded connection, or mechanical fastening such as screws, nails, bolts, etc. The tubing interface portions 218a, 218b and 228a, 228b may be the same or different depending on the application.

In some embodiments, the external system interfaces 261, 271, 281, 291 may also include an engagement region or pump interface portion 263, 273, 283, 293, as shown in FIGS. 26B and F, 27B and F, 28B and E, and 29B and E. The pump interface portion 263, 273, 283, 293 may be a section of the external system interface 261, 271, 281, 291 having a smaller diameter than the surrounding areas, as shown in FIGS. 26B and F, 27B and F, 28B and E, and 29B and E. The pump interface portion 263, 273, 283, 293 may be enclosed on either side by flanges. In some embodiments, the flanges help to secure the external system interface 261, 271, 281, 291 within a notch formed in the pump head housing. Upon installation of the tubing assembly within the pump head housing, the external system interface 261, 271, 281, 291 may be inserted into the notch on the pump head housing defined by flanges (not shown). The flanges sit within the pump interface portion 263, 273, 283, 293 to hold the external system interface 261, 271, 281, 291 in place. Additional details of the insertion of the external system interface within the pump head housing defined by flanges may be seen in FIGS. 20 and 21 of U.S. patent application Ser. No. 14/195,678, entitled "HIGH PRESSURE, HIGH FLOW RATE TUBING ASSEMBLY AND ADAPTER FOR A POSITIVE DISPLACEMENT PUMP," filed on Mar. 3, 2014, which is hereby incorporated by reference in its entirety.

As illustrated in FIGS. 30-33, each of the end fittings or tube interface portions 301, 311, 321, and 331 define a cylindrical passage 305, 315, 325, 335 through which fluid can pass to or from an inlet or outlet tube of the peristaltic pump. As discussed above, each of the end fittings 301, 311, 321, 331 are configured to connect with the external system interface of the tubing assembly, such as external system interfaces 281 and 291 illustrated in FIGS. 28 and 29.

FIG. 23 illustrates various views of a pump tubing gripper/lock, according to one embodiment. A rear perspective view of the pump tubing gripper/lock 231 is shown in FIG. 23A. The pump tubing gripper/lock 231 shown has two prongs or barbs 232a, 232b that fit within the ends of the peristaltic pump tubing, such as tubing 202 or 212 shown in FIGS. 20 and 21. The prongs or barbs 232a, 232b define cylindrical chambers 233a, 233b through which fluid can flow into the peristaltic pump tubing. The pump tubing gripper/lock 231 preferably provides a secure seal with the inner surface of the lumens of the tubing. As shown in FIG. 23A, a surface 237 of the pump tubing gripper/lock 231 defines a cap receiving space 236 configured to receive a cap such as cap 251, discussed in greater detail below. Preferably, stabilizer openings 234a, 234b are formed in the outer surface 237 of the pump tubing gripper/lock 231. The openings 234a, 234b may be disposed 180 degrees apart around the outer circumference of the pump tubing gripper/lock 231. The openings 234a, 234b are preferably configured to each accept a stabilizing pin (not shown). The stabilizing pins may be used to hold and stabilize the tubing assembly within a mold during the overmolding process. Additionally, in some embodiments, including the illustrated embodiment, the pump tubing gripper/lock 231 defines an interior recessed portion 235 located between the two fluid chamber openings 233a, 233b, as shown in FIG. 23B. The recessed portion 235 preferably assists with fluid diffusion and flow through the tubing of the peristaltic pump. The pump tubing gripper/lock 231 can include a channel or groove 239 (e.g., an exterior annular groove). The groove 239 can be defined by at least first and second interface surfaces portions. The groove 239 can be configured to cooperate (e.g., in an interference fit) with a flange or protrusion 209 (FIG. 20C) of the adapter/external system interface 206a, 206b. The flange or protrusion 209 can be defined by at least third and fourth interface surface portions. In a preferred embodiment, such as the illustrated embodiment, the pump tubing gripper/lock 231 may be formed from polyvinylidene fluoride (PVDF) or Kynar, a highly non-reactive and pure thermoplastic fluoropolymer. In other embodiments, the pump tubing gripper/lock 231 could be formed from other materials such as other types of polymer, metal, etc.

Another embodiment of a pump tubing gripper/lock is shown in FIG. 24. A rear perspective view of the pump tubing gripper/lock 241 is shown in FIG. 24A. The pump tubing gripper/lock 241 shown has two prongs or barbs 242a, 242b that fit within the ends of the peristaltic pump tubing, such as tubing 202 or 212 shown in FIGS. 20 and 21. In other embodiments, a pump tubing gripper/lock may have a single prong or barb or multiple prongs or barbs, depending on the number of lumens used for the tubing of the peristaltic pump. The prongs or barbs 242a, 242b define cylindrical chambers 243a, 243b through which fluid can flow into the peristaltic pump tubing. The pump tubing gripper/lock 241 preferably provides a secure seal with the inner surface of the lumens of the tubing. As shown in FIG. 24A, a surface 247 of the pump tubing gripper/lock 241 defines a cap receiving space 246 configured to receive a cap such as cap 251, discussed in greater detail below. Preferably, stabilizer openings 244a, 244b are formed in the outer surface 247 of the pump tubing gripper/lock 241. The openings 244a, 244b may be disposed 180 degrees apart around the outer circumference of the pump tubing gripper/lock 241. The openings 244a, 244b are preferably configured to each accept a stabilizing pin (not shown). The stabilizing pins may be used to hold and stabilize the tubing assembly within a mold during the overmolding process. Additionally, in some embodiments, including the illustrated embodiment, the pump tubing gripper/lock 241 defines an interior recessed portion 245 located between the two fluid chamber openings 243a, 243b, as shown in FIG. 24B. The recessed portion 245 preferably assists with fluid diffusion and flow through the tubing of the peristaltic pump. The pump tubing gripper/lock 241 can include a channel or groove 249 (e.g., an exterior annular channel or groove). The groove 249 can be defined by at least first and second interface surfaces portions. The groove 239 can be configured to cooperate (e.g., in an interference fit) with the flange or protrusions 209 (FIG. 20C) of the adapter/external system interface 206a, 206b. Similar to the gripper 231 discussed above, the pump tubing gripper/lock 241 may be formed from polyvinylidene fluoride (PVDF), a highly non-reactive and pure thermoplastic fluoropolymer. In other embodiments, the pump tubing gripper/lock 241 could be formed from other materials such as other types of polymer, metal, etc.

FIG. 25 illustrates one embodiment of a cap for an overmolded tubing assembly such as the tubing assembly 201, 211, and 212 shown in FIGS. 20A and B, 21A and B, and 22A and B. The cap 251 may be inserted within the cap receiving space 236, 246 of the pump tubing gripper/lock 231 or 241 to stabilize and maintain the diameter of the tubing gripper/lock assembly within the mold during the overmolding process. The caps 251 may also provide an open chamber for diffusing fluid into the tubing assembly. The cap 251 defines an outer surface 252 and an inner surface 253. When installed within a peristaltic pump tubing assembly, the inner surface 253 faces the tube gripper lock, as shown in the tubing assemblies 201, 211, and 221 illustrated in FIGS. 20B, 21B, and 22B. A cylindrical opening 254 is formed through the cap 251 to allow fluid flow through the cap 251. As shown in FIGS. 25C and D, two fluid directing ramps 255a and 255b extend from the inner surface 253 and flank the cylindrical opening 254. The fluid directing ramps 255a, 255b help to direct and diffuse fluid into the tubing through the tubing gripper/lock. In a preferred embodiment, the cap 251 is formed from polyvinylidene fluoride (PVDF), a highly non-reactive and pure thermoplastic fluoropolymer. In other embodiments, the cap 251 could be formed from other materials such as other polymer types, metal, etc.

Figure 34:
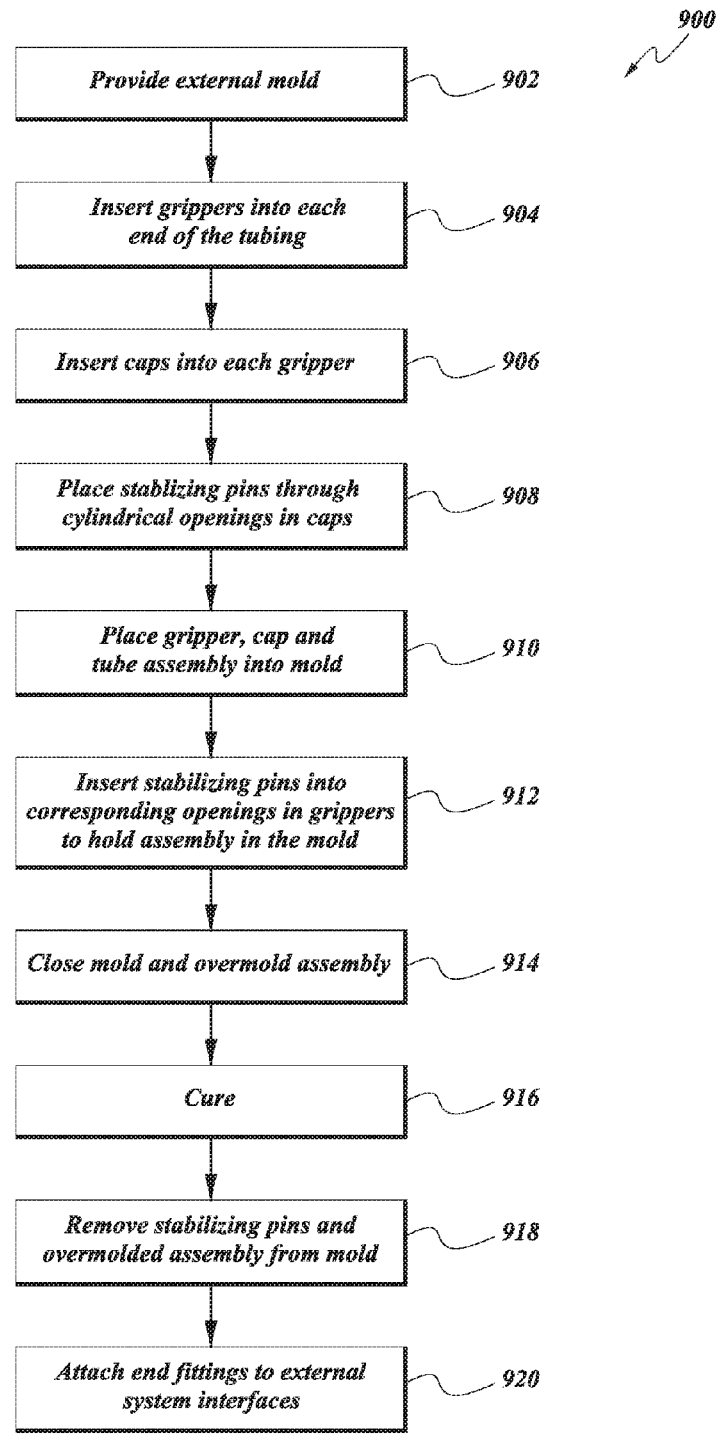
FIG. 34 illustrates a method of manufacturing an overmolded tubing assembly for a peristaltic pump, according to one embodiment.

In some embodiments, the following process, illustrated in FIG. 34, illustrates one method of manufacturing the overmolded peristaltic pump tubing assembly shown in FIGS. 20A and B. In the first step 902 of process 900, a mold is provided. Next, in step 904, previously formed pump tubing gripper/locks, such as locks 203a and 203b, are inserted within the first and second ends of the tubing 202 such that a tight fit is achieved between the locks 203a, 203b and the ends of the tubing. In one embodiment, if a single lumen tube is selected, a pump tubing gripper/lock configured to receive a single lumen tube is selected. If multiple lumen tubing is selected, a corresponding multiple lumen pump tubing gripper/lock configured to receive multiple lumen tubing may be selected, such as pump tubing gripper/locks 231, 241 shown in FIGS. 23 and 24. Different pump tubing gripper/lock inserts may be used, depending on the tubing profile. Next, as illustrated by step 906, caps, such as caps 204a and 204b, are inserted within the respective pump tubing gripper/locks 203a, 203b. When inserted into the pump tubing gripper/lock 203a, the cap 204a forms an open chamber between the inner surface of the cap 204a and the interior of the pump tubing gripper/lock 203a. A similar open chamber is formed between the inner surface of the cap 204b and the pump tubing gripper/lock 203b. These chambers allow fluid to be dispersed into the lumens (either single lumen or multiple lumens) of the tubing. The caps 204a and 204b help to stabilize and maintain the shape of the grippers and the tube assembly when it is next placed into the mold. In step 908, a set of mold stabilization pins (not shown) may be passed through the cylindrical opening of each of the caps 204a, 204b. These mold stabilization pins prevent polymer from clogging the cylindrical openings in the caps 204a, 204b and provide further support for the tubing assembly 201 during the overmolding process. In step 910, the gripper, cap, and tubing assembly is placed within the mold.

Next, as shown in step 912, stabilizing pins (not shown) may be used to hold the tubing assembly 201 in place within the mold. As discussed above with respect to the pump tubing gripper/locks shown in FIGS. 23 and 24, stabilizer openings 207b, 207c are configured to accept stabilizing pins and firmly hold the tubing assembly 201 within the mold during the overmolding process. Two stabilizer openings 207b, 207c are shown in FIG. 20B; however, another set of stabilizer openings may be provided on an opposite side of each of the pump tubing gripper/locks 203a, 203b, as illustrated in FIGS. 23 and 24.

Once the tubing 202, pump tubing gripper/locks 203a, 203b, and caps 204a, 204b have been placed in the mold, the mold is closed as shown in step 914 and the adapter/external system interfaces 206a, 206b are molded over the existing assembly in an overmolding process. Once formed, the openings 207a and 207d in the adapter/external system interfaces 206a, 206b will align with the openings 207b, 207c in the pump tubing gripper/locks 203a, 203b as the molding material flows and forms over the ends of the tubing assembly 201. As illustrated in FIG. 20, a tubing interface portion 208a, 208b may be molded with the external system interfaces 206a, 206b as a single piece. In other embodiments, such as those shown in FIGS. 21A, B and 22A, B, the tubing interface portions may be secured to the external system interfaces after the overmolding process. Preferably, the overmolded adapter/external system interfaces 206a, 206b extend along the longitudinal length of the tubing beyond the ends of the tubing 202. In a preferred embodiment, the adapter/external system interface 206a, 206b is formed from polyvinylidene fluoride (PVDF), which preferably does not bond to the tubing material. As the overmolded adapter/external system interface 206a, 206b cures and cools, as shown in step 916, the interfaces 206a, 206b shrink, clamping down on the external surface of the tubing 202 and the pump tubing gripper/locks 203a, 203b, forming a tight external, mechanical seal and not a fusion or chemical bond. The overmolded adapter wraps around the multi-tube design to preferably form a perfect fit with the external surface of the tubing and the gripper/lock and during cooling/curing, shrinks to an ideal seal with the external surface of the tubing. Thus, a mechanical seal between the overmolded adapter and the tubing is created as opposed to a material bond or fusion between the overmolded adapter and the tubing. Once the overmolding process is complete, the stabilizing pins may be removed, as shown in step 918. In some embodiments, as illustrated by step 920, an end fitting or tube interface portion such as those shown in FIGS. 30-33 may be spin welded or otherwise attached to the overmolded adapter/external system interface 206a, 206b. The external system interface and the tubing interface portions may be connected by any of a number of connecting methods, including spin welding, sonic welding, glue or other adhesion, threaded connection via O-ring, or the pieces may screwed together using one or more screws or other mechanical fasteners. In some embodiments, the same external system interface 261, 271, 281, 291 may be used on both the first and second ends of the tubing assembly. In other embodiments, different external system interfaces 261, 271, 281, 291 may be used on the first and second ends of the tubing assembly. Once the adapter system is fully assembled with the tube 202, the tubing assembly may be installed within the pump head or housing configured with peristaltic pump roller, similar to that shown in FIGS. 16-18. However, the tubing assembly described above may be used with any number of peristaltic pump assemblies, such as but not limited to single roller or multiple roller assemblies.

A similar process as discussed above with respect to FIG. 34 applies to the formation and assembly of tubing assemblies 211 and 221 shown in FIGS. 21A, B and 22A, B.

Figure 37:
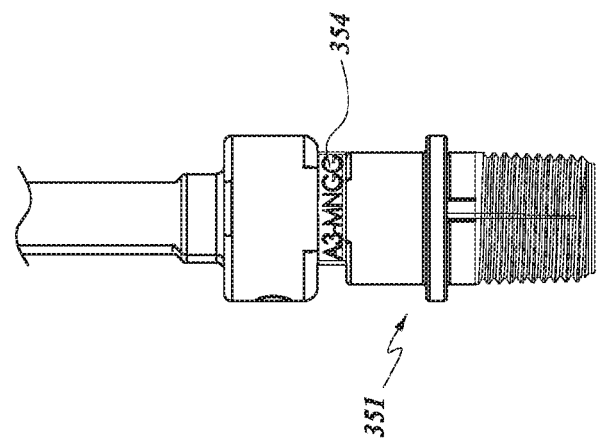
FIG. 37 illustrates a detailed view of a tubing identifier and adapter assembly of the peristaltic tubing assembly of FIG. 35.
Figure 36:
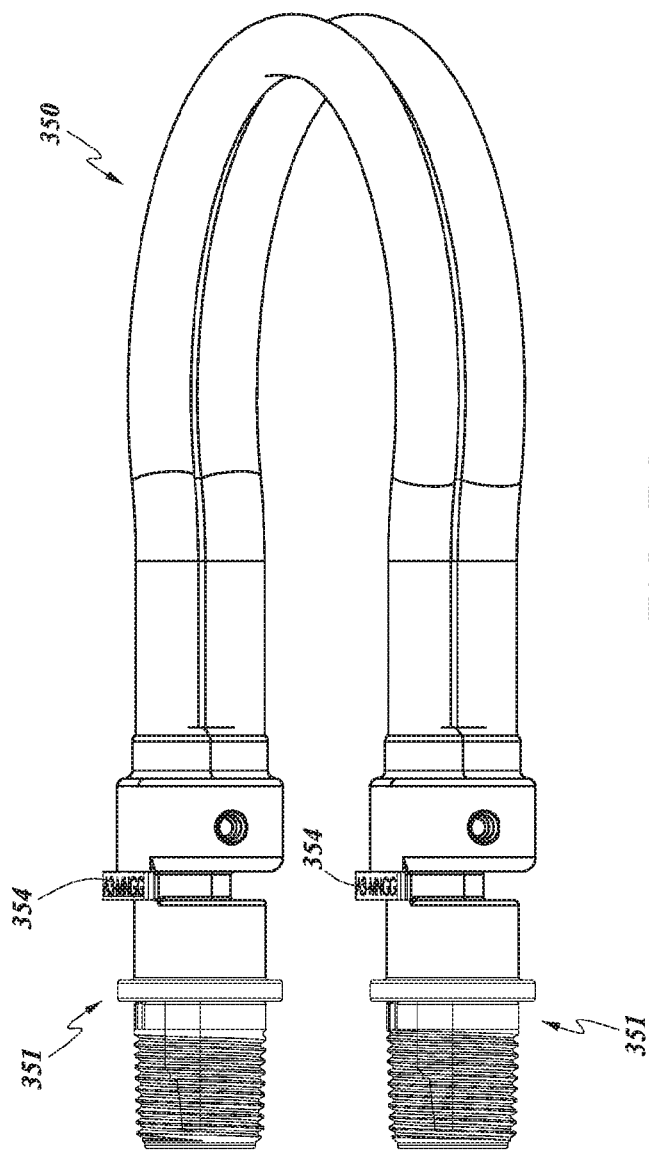
FIG. 36 illustrates a side view of the peristaltic tubing assembly shown in FIG. 35.

FIGS. 35-37 illustrate another embodiment of a tubing assembly for a peristaltic pump. The tubing assembly 350 may include a tube identifier portion 354 that may be located on an adapter assembly 351 of the tubing assembly 350. The tubing identifier portion 354 may be formed integrally with the adapter assembly 351 or may be a tab or other additional piece that may be clipped or adhesively attached to the adapter assembly 351 or to any other part of the tubing assembly 350. The tube identifier portion 354 may be preprinted with identification indicia, such as numerals and/or letters identifying, for example, the tubing assembly 350, such as the size of the tube, pump size, tube material, adapter connection type, etc.

Figure 38:
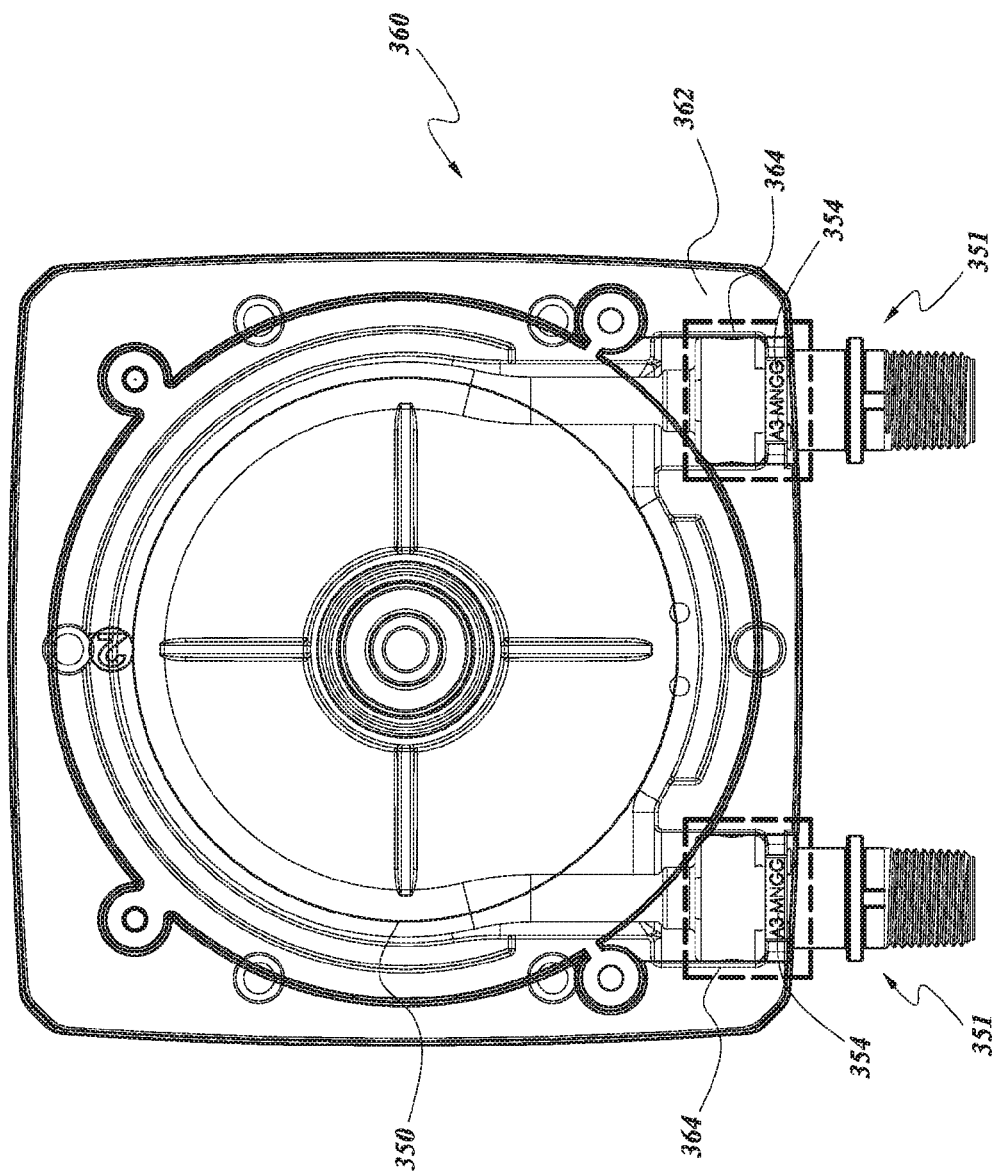
FIG. 38 illustrates a peristaltic pump having a tubing assembly formed in accordance with the principles disclosed herein, according to another embodiment.

The tubing assembly 350 shown in FIGS. 35-37 may be used with a peristaltic pump such as that shown in FIGS. 38-39. The pump 360 preferably includes a pump cover 362 formed of a clear or transparent material such that the tubing 350 and the tube identifier portion 354 may be viewed through the cover 362 to easily identify the type of tubing and/or connector used in the peristaltic pump tubing assembly. In some embodiments, the cover 362 may include a magnifying portion 364 preferably located above the tube inlet and outlet ports such that the magnifying portion 364 can magnify the tube identifier portion 354 located on the adapter assembly 351, such that a person viewing the adaptor from the outside will view a magnified image of the identifier portion 354, such as the identification indicia.

In addition to the single and dual tubes or lumens discussed above, other single or multiple lumen tubing profiles may be used in other tubing assembly embodiments. For example, in some embodiments, a dual tubing or lumen profile such as those shown in FIGS. 7-14, may be used with the peristaltic pump assembly discussed above.

The tubing assemblies discussed above may be manufactured with various combinations of tubing interface portions and external system interfaces, depending on the tubing profile (for example, single or multiple lumen tubing) and/or customer requirements. Four different external system interfaces 261, 271, 281, 291 and four different end fittings or tubing interface portions 301, 311, 321, 331 are shown in FIGS. 26-33. Two of the external system interfaces 281, 291 may be paired with each tubing interface portion 301, 311, 321, 331 to provide at least 8 manufactured tubing assembly configurations, depending on the tubing diameter and profile as well as customer requirements. The adapters illustrated in FIGS. 26-33 are examples only and are not meant to illustrate the full range of adapter configurations possible for a tubing assembly. The external system interfaces best illustrated in FIGS. 26-29 are configured to engage with flanges that form notches on a peripheral edge of the pump housing. As discussed above, each of the external system interfaces has an engagement region or pump interface portion that in some embodiments may be an external groove formed in the body of the external system interface having approximately the same width as the flanges of the pump head. The external system interfaces may be inserted within the notches formed in the pump head housing such that the flanges of the pump head housing engage with the engagement regions of the external system interfaces to form a secure fit. Once installed, the end of the external system interface connected to the tubing assembly of the peristaltic pump is located within the pump housing while the opposite end of the external system interface is located outside the pump head housing.

Embodiments of the tubing assemblies disclosed herein can be fabricated using a variety of materials, such as polymer materials, rubber, polyurethane, neoprene, tygothane, and others. Further, the tubing assemblies can be fabricated as a composite of multiple materials, or monolithically or uniformly using a single material. Embodiments of the external system interfaces and tube mounts disclosed herein may be manufactured from plastics.

Although embodiments of these inventions have been disclosed in the context of certain examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions.

What is claimed is:

1. A tubing and adapter assembly for a peristaltic pump, the tubing and adapter assembly comprising:
    an elongate body defining a longitudinal axis, a first end, and a second end, the elongate body having a plurality of lumens extending along the longitudinal axis, each lumen being surrounded by a tube wall, the plurality of lumens extending from the first end to the second end such that the first end is in fluid communication with the second end of the elongate body;
    a first tube gripper having a plurality of prongs defining cylindrical openings such that each of said plurality of prongs grips an interior surface of a tube wall defining one of the plurality of lumens adjacent said first end of the body;
    a second tube gripper having a plurality of prongs defining cylindrical openings such that each of said plurality of prongs grips an interior surface of a tube wall defining one of the plurality of lumens adjacent said second end of the body, the first tube gripper and the second tube gripper each defining an external annular groove;
    a first external system interface having an annular surface defining a first flow passage, a first tubing interface portion, a first pump interface portion sized and shaped to cooperate with said peristaltic pump to position the first pump interface portion relative said peristaltic pump, and a first mounting interface portion; and
    a second external system interface having an annular surface defining a second flow passage, a second tubing interface portion, a second pump interface portion sized and shaped to cooperate with said peristaltic pump to position the second pump interface portion relative said peristaltic pump, and a second mounting interface portion;
    wherein the first and second external system interfaces are respectively molded over the first and second tube grippers such that a protrusion forms inside their respective grooves forming an interference fit connection which prevents any movement of the first and second external system interface system relative to its associated tube gripper, and which molding also forms a seal on an exterior surface of the tube walls defining the plurality of lumens, said first and second external system interfaces having a mechanical seal around the first and second tube grippers, respectively, and not a chemical bond, wherein said assembly is configured such that a rotor of the peristaltic pump can operate against the tubing and adapter assembly for pumping fluid through the tubing and adapter assembly.

2. The tubing and adapter assembly of claim 1, wherein the first external system interface is one of a hose barb adapter, threaded adapter, sanitary adapter, and quick-release adapter.

3. The tubing and adapter assembly of claim 1, wherein the first external system interface is the same type of interface as the second external system interface.

4. The tubing and adapter assembly of claim 1, wherein a first tubing interface is coupled to the first external system interface by one of spin welding, sonic welding, glue, threaded connection, and one or more mechanical fasteners.

5. The tubing and adapter assembly of claim 1, wherein the assembly comprises three lumens.

6. The tubing and adapter assembly of claim 1, wherein the assembly comprises a pair of tubes that are fused together.

7. The tubing and adapter assembly of claim 1, wherein the assembly comprises three tubes that are fused together.

8. The tubing and adapter assembly of claim 1, wherein the assembly comprises a plurality of tubes that are interconnected longitudinally by a coupling.

9. The tubing and adapter assembly of claim 8, wherein the coupling extends between a given pair of tubes of the plurality of tubes.

10. The tubing and adapter assembly of claim 9, wherein the plurality of tubes may be separated by tearing the coupling.

11. The tubing and adapter assembly of claim 1, wherein the assembly comprises a pair of separate tubes.

12. The tubing and adapter assembly of claim 1, further comprising a tube identifier portion.

13. The tubing and adapter assembly of claim 12, wherein the tube identifier portion extends from one side of the tubing and adapter assembly such that the tube identifier portion is readable when the tubing and adapter assembly is installed in the peristaltic pump.

14. A tubing and adapter assembly for a peristaltic pump, the tubing and adapter assembly comprising:
    an elongate body defining a longitudinal axis, a first end, and a second end, the elongate body having a plurality of lumens extending along the longitudinal axis, each lumen being surrounded by a tube wall, the plurality of lumens extending from the first end to the second end such that the first end is in fluid communication with the second end of the elongate body;
    a first tube gripper having a plurality of prongs defining cylindrical openings such that each of said plurality of prongs grips an interior surface of a tube wall defining one of the plurality of lumens adjacent said first end of the body;
    a second tube gripper having a plurality of prongs defining cylindrical openings such that each of said plurality of prongs grips an interior surface of a tube wall defining one of the plurality of lumens adjacent said second end of the body, the first tube gripper and the second tube gripper defining a first interference surface portion and a second interference surface portion, respectively;
    a first external system interface having an annular surface defining a first flow passage, a first tubing interface portion, a first pump interface portion sized and shaped to cooperate with said peristaltic pump to position the first pump interface portion relative said peristaltic pump, and a first mounting interface portion; and
    a second external system interface having an annular surface defining a second flow passage, a second tubing interface portion, a second pump interface portion sized and shaped to cooperate with said peristaltic pump to position the second pump interface portion relative said peristaltic pump, and a second mounting interface portion;

wherein the first and second external system interfaces are molded over the first and second tube grippers respectively (1) to form a third interference surface portion and fourth interference surface portion, said first interference surface portion and said third interference surface portion cooperating to prevent relative movement of the first external interface relative to the first tube gripper in a first direction along the longitudinal axis and said second interference surface portion and said fourth interference surface portion cooperating to prevent relative movement of the first external interface relative to the first tube gripper in a second direction along the longitudinal axis, and (2) to form a seal on an exterior surface of the tube walls defining the plurality of lumens, said first and second external system interfaces forming a mechanical seal and not a chemical bond with said first and second tube grippers respectively and said assembly configured such that a rotor of the peristaltic pump can operate against the tubing and adapter assembly for pumping fluid through the tubing and adapter assembly.

15. The tubing and adapter assembly of claim 14, wherein the first external system interface is one of a hose barb adapter, threaded adapter, sanitary adapter, and quick-release adapter.

16. The tubing and adapter assembly of claim 14, wherein the second external system interface is one of a hose barb adapter, threaded adapter, sanitary adapter, and quick-release adapter.

17. The tubing and adapter assembly of claim 14, wherein the first external system interface is the same type of interface as the second external system interface.

18. The tubing and adapter assembly of claim 14, wherein a first tubing interface is coupled to the first external system interface by one of spin welding, sonic welding, glue, threaded connection, and one or more mechanical fasteners.

19. The tubing and adapter assembly of claim 14, wherein a second tubing interface is coupled to the second external system interface by one of spin welding, sonic welding, glue, threaded connection, and one or more mechanical fasteners.

20. The tubing and adapter assembly of claim 14, wherein the assembly comprises two lumens.

21. The tubing and adapter assembly of claim 14, wherein the assembly comprises a pair of tubes that are fused together.

22. The tubing and adapter assembly of claim 14, wherein the assembly comprises three tubes that are fused together.

23. The tubing and adapter assembly of claim 14, wherein the assembly comprises a plurality of tubes that are interconnected longitudinally by a coupling.

24. The tubing and adapter assembly of claim 23, wherein the coupling extends between a given pair of tubes of the plurality of tubes.

25. The tubing and adapter assembly of claim 24, wherein the plurality of tubes may be separated by tearing the coupling.

26. The tubing and adapter assembly of claim 14, wherein the assembly comprises a pair of separate tubes.

27. The tubing and adapter assembly of claim 14, further comprising a tube identifier portion.

28. The tubing and adapter assembly of claim 27, wherein the tube identifier portion extends from one side of the tubing and adapter assembly such that the tube identifier portion is readable when the tubing and adapter assembly is installed in the peristaltic pump.

* * * * *